US012004774B2

United States Patent
Thompson et al.

(10) Patent No.: US 12,004,774 B2
(45) Date of Patent: Jun. 11, 2024

(54) GAS CIRCULATION SYSTEM WITH GAS SEALED ACCESS CAP AND VALVE SEALED ACCESS CAP FOR ROBOTICALLY ASSISTED SURGICAL PROCEDURES

(71) Applicant: Conmed Corporation, Largo, FL (US)

(72) Inventors: Emily Thompson, Castle Rock, CO (US); Corey London Brenner, Littleton, CO (US)

(73) Assignee: Conmed Corporation, Largo, FL (US)

( * ) Notice: Subject to any disclaimer, the term of this patent is extended or adjusted under 35 U.S.C. 154(b) by 182 days.

(21) Appl. No.: 17/841,865

(22) Filed: Jun. 16, 2022

(65) Prior Publication Data

US 2022/0304724 A1    Sep. 29, 2022

Related U.S. Application Data

(63) Continuation of application No. 16/829,694, filed on Mar. 25, 2020, now Pat. No. 11,399,866.

(60) Provisional application No. 62/925,424, filed on Oct. 24, 2019, provisional application No. 62/876,141, filed on Jul. 19, 2019, provisional application No. 62/823,848, filed on Mar. 26, 2019.

(51) Int. Cl.
| | |
|---|---|
| *A61B 17/34* | (2006.01) |
| *A61B 17/00* | (2006.01) |
| *A61B 34/00* | (2016.01) |
| *A61B 34/30* | (2016.01) |

(52) U.S. Cl.
CPC .... *A61B 17/3423* (2013.01); *A61B 17/00234* (2013.01); *A61B 17/3462* (2013.01); *A61B 17/3498* (2013.01); *A61B 34/30* (2016.02); *A61B 34/70* (2016.02); *A61B 2017/3464* (2013.01)

(58) Field of Classification Search
CPC .................................. A61B 17/3423
See application file for complete search history.

(56) References Cited

U.S. PATENT DOCUMENTS 7,854,724 B2    12/2010  Stearns et al.
8,795,223 B2 *   8/2014  Stearns .............. A61B 17/3462
                                              604/167.03

(Continued)

OTHER PUBLICATIONS

International Search Report issued in corresponding PCT Patent Application No. PCT/US2020/024711, dated Jul. 10, 2020.

(Continued)

*Primary Examiner* — Christian A Sevilla
(74) *Attorney, Agent, or Firm* — Locke Lord LLP; Scott D. Wofsy

(57) ABSTRACT

A gas circulation system is disclosed for performing robotically assisted surgical procedures in a surgical cavity of a patient, which includes a multi-lumen tube set including a dual lumen portion having a pressurized gas line and a return gas line, and a single lumen portion having a gas supply and sensing line, a valve sealed access cap for cooperative reception with a first robotic cannula and having an inlet path for communicating with the gas supply and sensing line of the tube set, and a gas sealed access cap for cooperative reception with a second robotic cannula and having an inlet path for communicating with the pressurized gas line of the tube set and an outlet path for communicating with the return gas line of the tube set.

20 Claims, 23 Drawing Sheets

(56) References Cited

U.S. PATENT DOCUMENTS

| | | | |
|---|---|---|---|
| 9,067,030 B2 | 6/2015 | Stearns et al. | |
| 9,375,539 B2 | 6/2016 | Stearns et al. | |
| 9,526,886 B2 | 12/2016 | Mastri et al. | |
| 10,463,395 B2 | 11/2019 | Reid et al. | |
| 2004/0204671 A1 | 10/2004 | Stubbs et al. | |
| 2005/0004512 A1 | 1/2005 | Campbell et al. | |
| 2005/0015043 A1 | 1/2005 | Stubbs et al. | |
| 2006/0149305 A1 | 7/2006 | Cuevas et al. | |
| 2007/0088275 A1 | 4/2007 | Stearns et al. | |
| 2010/0256567 A1 | 10/2010 | Smith | |
| 2013/0253278 A1* | 9/2013 | Smith | A61B 17/0293 600/204 |
| 2013/0303848 A1 | 11/2013 | Kahle et al. | |
| 2014/0074015 A1 | 3/2014 | Mastri et al. | |
| 2014/0088491 A1 | 3/2014 | Azarbarzin et al. | |
| 2014/0171855 A1 | 6/2014 | Mastri et al. | |
| 2014/0188038 A1 | 7/2014 | Stearns et al. | |
| 2014/0309583 A1 | 10/2014 | Stearns et al. | |
| 2014/0358070 A1 | 12/2014 | Stearns et al. | |
| 2015/0031958 A1* | 1/2015 | Kleyman | A61B 17/3462 600/204 |
| 2018/0256207 A1 | 9/2018 | Augelli et al. | |
| 2018/0256830 A1 | 9/2018 | Silver et al. | |
| 2019/0167967 A1* | 6/2019 | Mottola | A61M 25/09 |
| 2020/0205855 A1* | 7/2020 | Aravalli | A61B 17/3496 |
| 2020/0305928 A1 | 10/2020 | Thompson et al. | |
| 2021/0015572 A1 | 1/2021 | Gomez et al. | |
| 2021/0244436 A1 | 8/2021 | Desjardin et al. | |

OTHER PUBLICATIONS

International Preliminary Report on Patentability and Written Opinion of the International Searching Authority dated Jul. 10, 2020, issued during the prosecution of International Patent Application No. PCT/US2020/024711.

Extended European Search Report dated Oct. 26, 2022, issued during the prosecution of European Patent Application No. EP 20778743.3.

PCT International Search Report and Written Opinion dated Nov. 24, 2022, issued during the prosecution of PCT International Application No. PCT/US2022/038628.

* cited by examiner

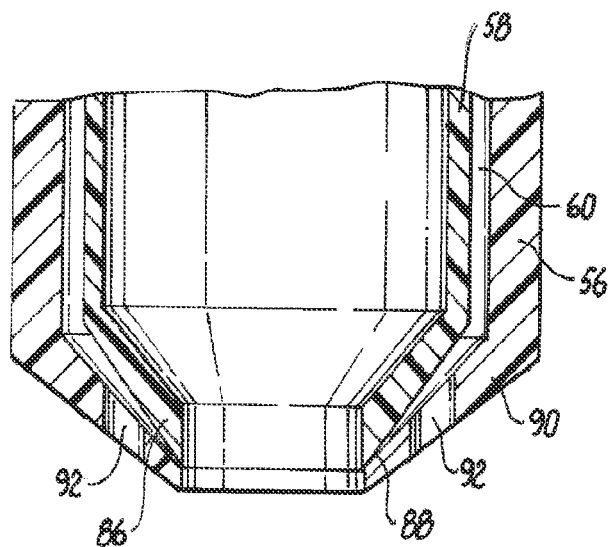
Fig. 9
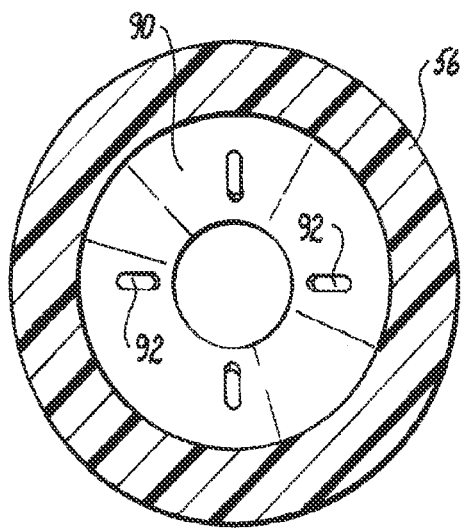 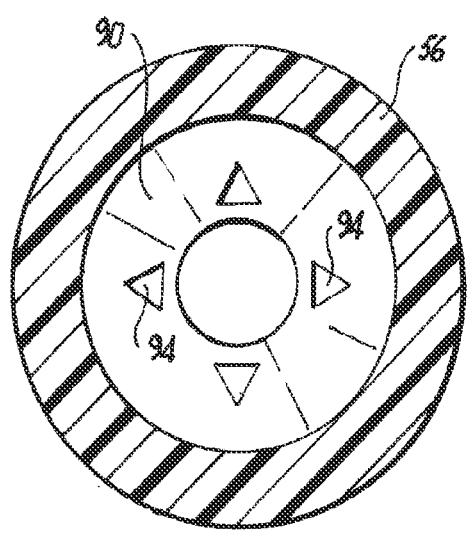
Fig. 10    Fig. 11

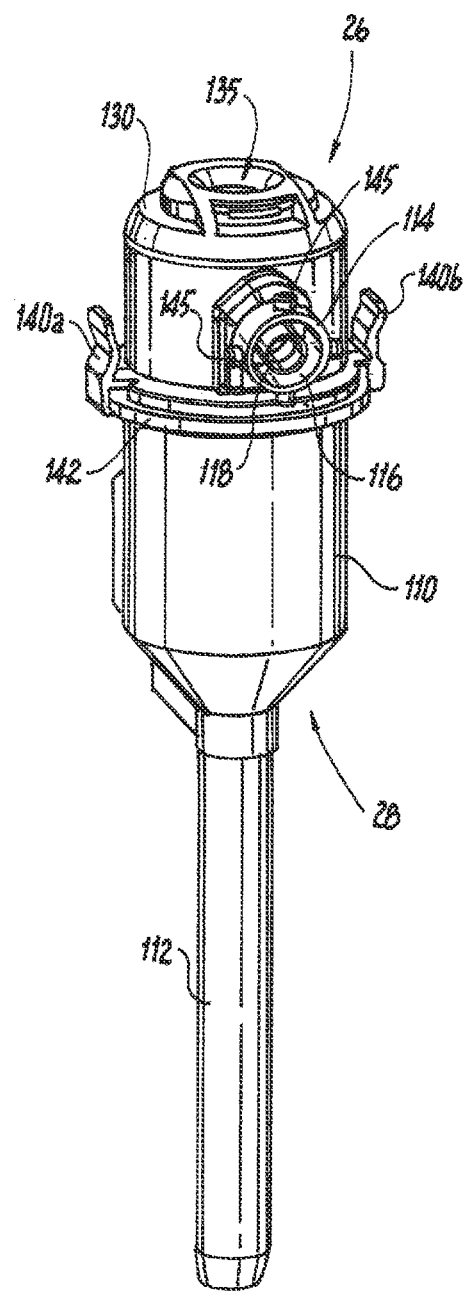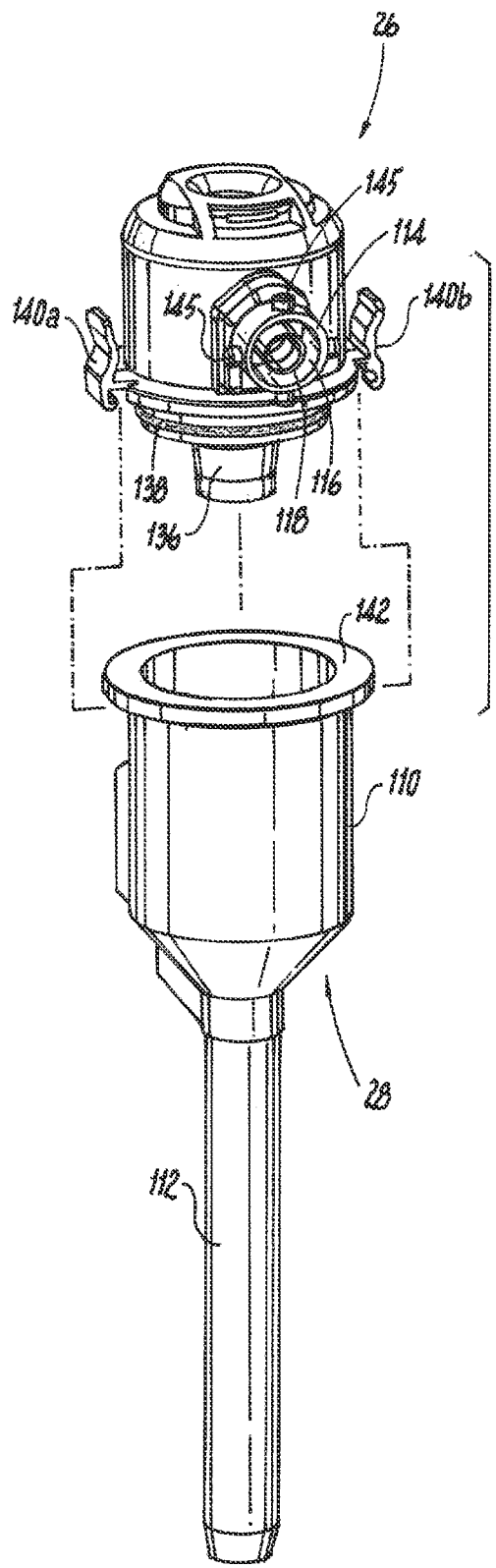
Fig. 16
Fig. 17

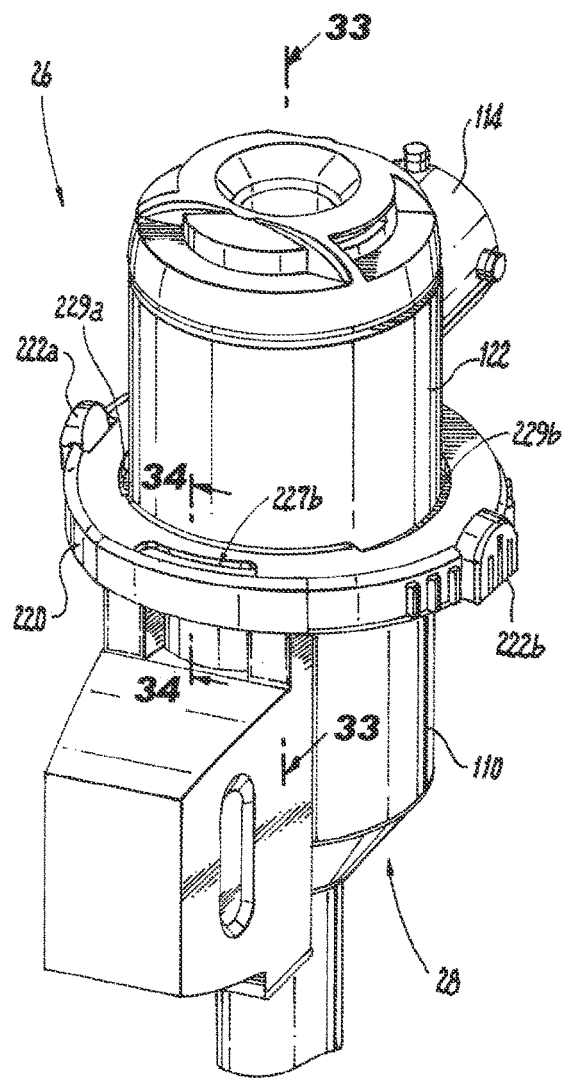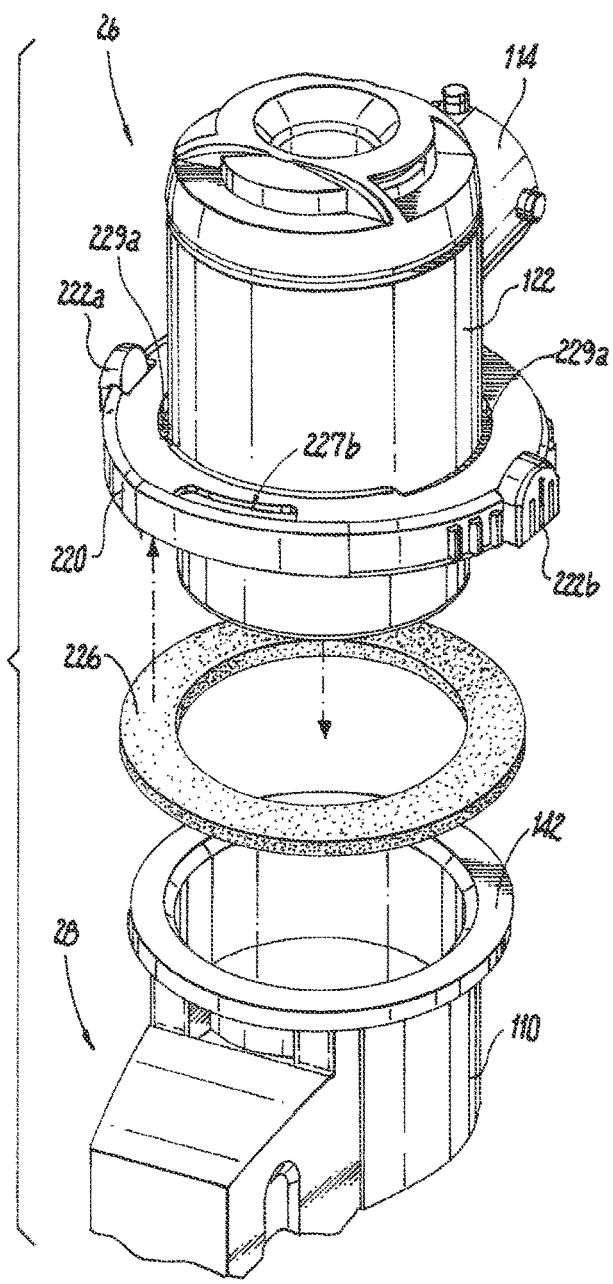
Fig. 31
Fig. 32

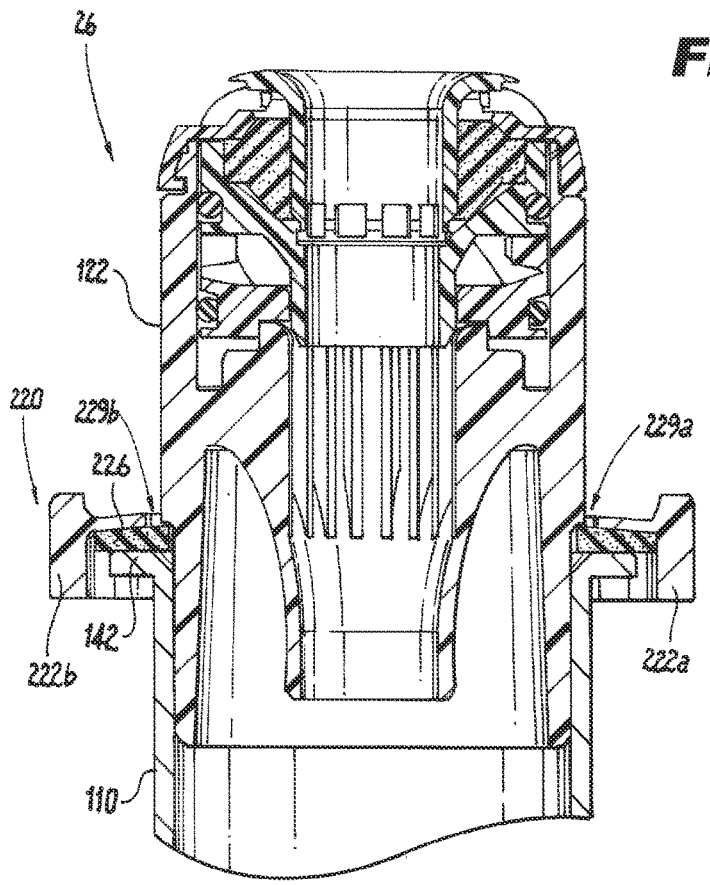
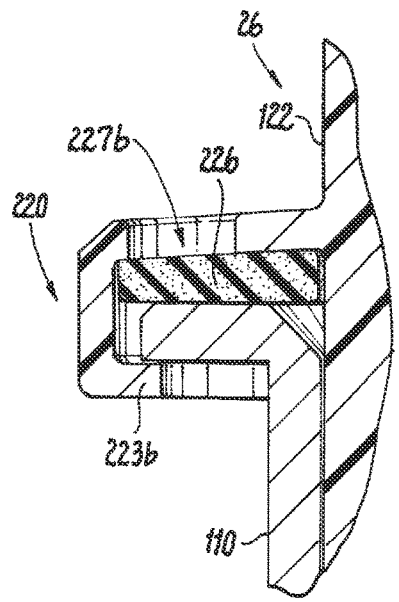
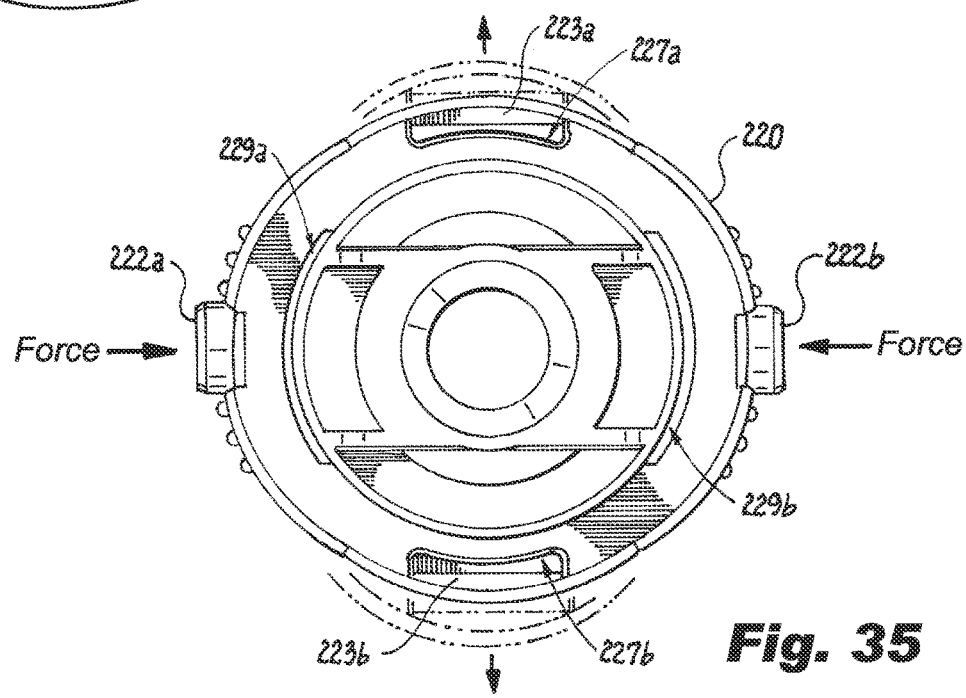
Fig. 34
Fig. 33
Fig. 35

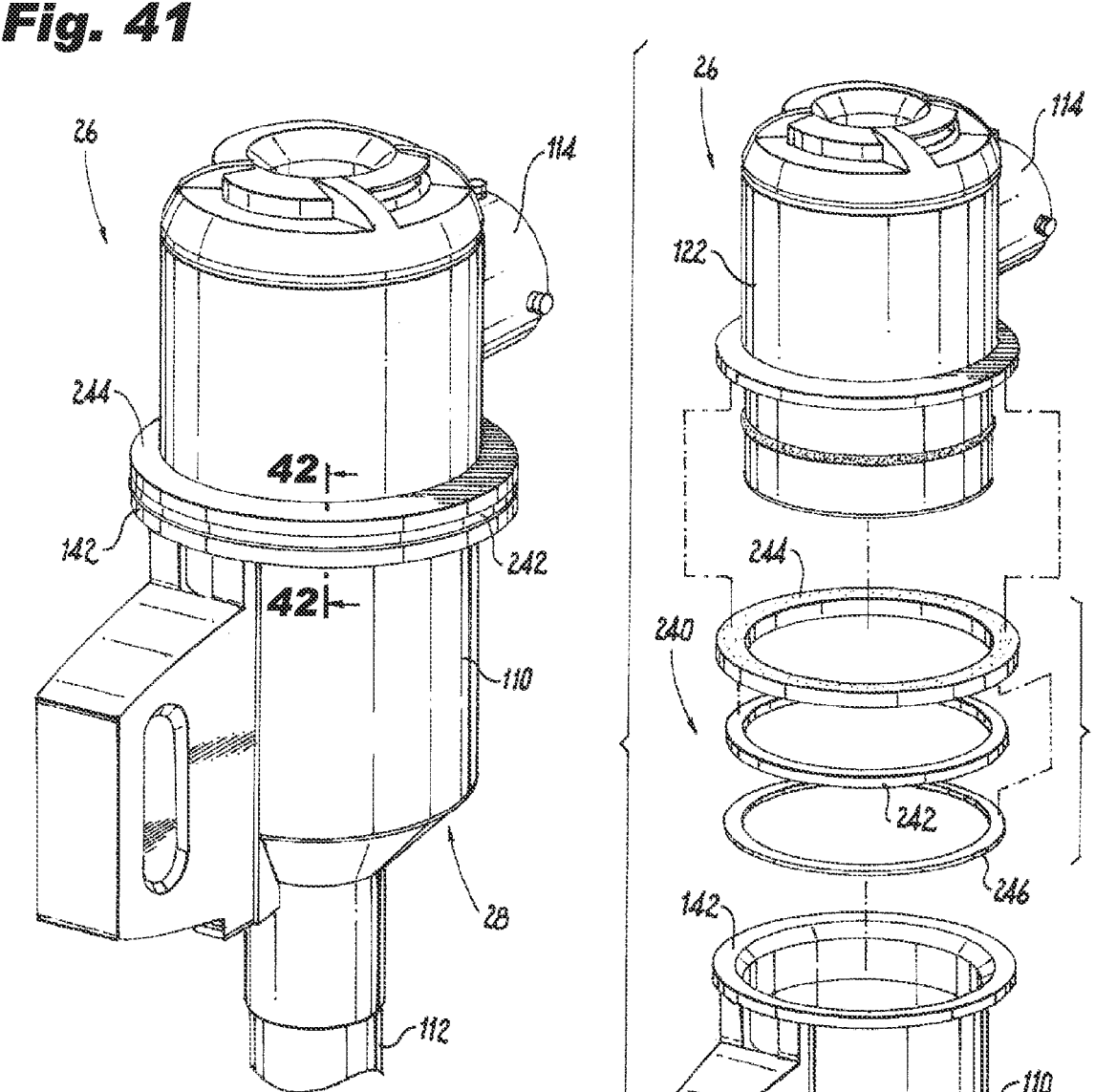
Fig. 41
Fig. 43
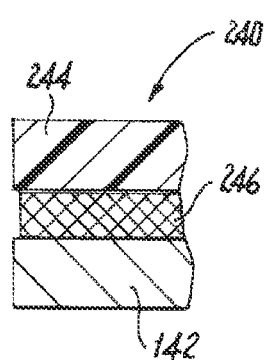
Fig. 42

GAS CIRCULATION SYSTEM WITH GAS SEALED ACCESS CAP AND VALVE SEALED ACCESS CAP FOR ROBOTICALLY ASSISTED SURGICAL PROCEDURES

CROSS-REFERENCE TO RELATED APPLICATION

This subject application in a Continuation of U.S. patent application Ser. No. 16/829,694, filed Mar. 25, 2020, which claims the benefit of priority to U.S. Provisional Patent Application Ser. No. 62/823,848 filed Mar. 26, 2019, U.S. Provisional Patent Application Ser. No. 62/876,141 filed Jul. 19, 2019, and U.S. Provisional Patent Application Ser. No. 62/925,424 filed Oct. 24, 2019, the disclosures of which are all herein incorporated by reference in their entireties.

BACKGROUND OF THE INVENTION

1. Field of the Invention

The subject invention is directed to endoscopic surgery, and more particularly, to a surgical gas circulation system with a gas sealed access cap and a valve sealed access cap for use during robotically assisted laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. No. 7,854,724. These devices are constructed from several nested components including an inner tubular body portion and a coaxial outer tubular body portion. The inner tubular body portion defines a central lumen for introducing conventional laparoscopic surgical instruments to the abdominal cavity of a patient and the outer tubular body portion defines an annular lumen surrounding the inner tubular body portion for delivering insufflation gas to the abdominal cavity of the patient and for facilitating periodic sensing of abdominal pressure.

Robotically assisted minimally invasive surgical procedures have also become increasingly more common. One well-known system for performing these procedures is called the Da Vinci robotic surgical system, which is manufactured and sold by Intuitive Surgical, Inc. of Sunnyvale, CA. The Da Vinci system utilizes a proprietary trocar or cannula that is adapted and configured to receive robotic instruments and be engaged by a robotic arm. The proprietary Da Vinci cannula has a proximal housing that forms a bowl for receiving components such as a gas-tight seal assembly, as disclosed for example in U.S. Pat. No. 10,463, 395. The Da Vinci gas-tight seal assembly utilizes mechanical seals to seal around an outer surface of surgical instruments passing through the cannula and to prevent the escape of insufflation gas from the abdominal cavity.

It is believed to be beneficial to provide a seal assembly for use with the Da Vinci cannula that permits ready access to an insufflated surgical cavity without the need for a mechanical seal assembly. Indeed, a recent example of such a pneumatic seal assembly is disclosed in commonly assigned U.S. Patent Application Publication No. 2018/0256207. The subject invention provides improvements to this earlier gas sealed access device, which are described in detail herein below, along with other novel devices and systems.

SUMMARY OF THE DISCLOSURE

The subject invention is directed to a new and useful gas circulation system for performing robotically assisted surgical procedures in a surgical cavity of a patient. The system includes a multi-lumen tube set having a dual lumen portion with a pressurized gas line and a return gas line for facilitating gas recirculation relative to the surgical cavity of the patient, and a single lumen portion with a gas supply and sensing line for delivering insufflation gas to the abdominal cavity of the patient and for periodically sensing pressure within the surgical cavity of the patient.

The system further includes a valve sealed access cap adapted and configured for cooperative reception within a proximal bowl portion of a first robotic cannula and having an inlet path for communicating with the gas supply and sensing line of the tube set, and a gas sealed access cap adapted and configured for cooperative reception within a proximal bowl portion of a second robotic cannula and having an inlet path for communicating with the pressurized gas line of the tube set and an outlet path for communicating with the return gas line of the tube set.

The valve sealed access cap includes an outer housing portion and an inner body portion, and an annular channel is formed between the outer housing portion and the inner body portion in communication with the inlet path. An inner O-ring seals the annular channel between the outer housing portion and the inner housing portion to prevent gas leakage.

The outer housing portion includes a pair of diametrically opposed flexible clips that are adapted and configured to be releasably latched to the proximal bowl portion of the first robotic cannula. An outer O-ring is positioned between the outer housing portion and the proximal bowl portion of the first robotic cannula to provide frictional engagement and prevent gas leakage therebetween.

The inner body portion of the valve sealed access cap supports a primary valve and a secondary valve. The primary valve is a circular septum valve and the secondary valve is a duckbill valve. The primary valve is located proximal to the secondary valve. A sound attenuating foam material is positioned within the valve sealed access cap proximal to the primary valve for reducing sound levels and to aid in holding the primary valve and secondary valve in place during instrument insertion, removal and manipulation.

A lid is engaged with a proximal end of the outer housing portion to secure the inner body portion within the outer housing portion and to provide security during instrument insertion, removal and manipulation. The lid further secures the inner body portion, the sound attenuating foam material, the primary valve and the secondary valve within the outer housing portion relative to the inner body portion.

Preferably, the inlet path is formed with the outer housing portion and a luer type connector is operatively associated therewith for communicating with the gas supply and sensing line of the tube set. The luer type connector is selectively sized to achieve a desired amount of gas flow into the inlet path.

A distal end surface of the inner body portion compressively engages against an interior distal surface of an inwardly tapered distal wall of the outer housing portion to enclose the annular channel. In one embodiment of the invention, the annular channel communicates with the proximal bowl portion of the first robotic cannula through a plurality of circumferentially spaced apart nares formed in the inwardly tapered distal wall of the outer housing portion. The plurality of nares can be oval shaped and extend radially outwardly from a central axis of the outer housing portion, or the plurality of nares can extend generally tangentially relative to a central axis of the outer housing portion. The nares could also be triangular shaped and extend radially outwardly from a central axis of the outer housing portion. Those skilled in the art will readily appreciate that the number and/or size of the nares can be selected to provide da desired gas flow.

In another embodiment of the invention, the annular channel communicates with the proximal bowl portion of the first robotic cannula through an annular nare that is defined between an inwardly tapered distal wall of the inner body portion and an inwardly tapered distal wall of the outer housing portion.

The gas sealed access cap includes a main housing portion defining an interior cavity that supports an annular jet assembly for receiving pressurized gas from the inlet path and for generating a gaseous sealing zone within the second robotic cannula to maintain a stable pressure within the surgical cavity of the patient. A sound attenuating foam material is positioned within the gas sealed access cap proximal to the annular jet assembly. A lid is engaged with a proximal end of the outer housing portion to secure the annular jet assembly and sound attenuating foam material within the main housing portion.

In addition, the main housing portion includes an integrally formed set of circumferentially spaced apart vanes for directing gas from the gaseous sealing zone to the outlet path of the gas sealed access cap. The set of circumferentially spaced apart vanes extend distally to form a tubular extension that extends into the proximal bowl portion of the second robotic cannula.

An outer O-ring is positioned between the main housing portion of the gas sealed access cap and the proximal bowl portion of the second robotic cannula. The inlet path and the outlet path of the gas sealed access cap communicate with a manifold associated with a bullseye connector fitting for communicating with the pressurized gas line and the return gas line of the tube set. The bullseye connector fitting has a plurality of circumferentially spaced apart radially outwardly extending engagement lugs formed thereon.

In one embodiment of the invention, the bullseye connector fitting is a bi-lumen bullseye connector fitting for communicating with the pressurized gas line and the return gas line of the tube set. In another embodiment, the bullseye connector fitting is a tri-lumen bullseye connector fitting for communicating with the pressurized gas line and the return gas line of the tube set, but not with the gas supply and sensing line of the tube set.

In one embodiment of the invention, the dual lumen portion of the tube set includes a coupling having circumferentially arranged bayonet type fastening channels formed therein for mechanically engaging with the engagement lugs of the bullseye connector fitting. In another embodiment of the invention, the dual lumen portion of the tube set includes a coupling having helically arranged bayonet type fastening channels formed therein for mechanically engaging with the engagement lugs of the bullseye connector fitting, In one embodiment of the invention, the main outer housing portion of the gas sealed access cap includes a pair of diametrically opposed flexible clips adapted and configured to be releasably latched to the proximal bowl portion of the second robotic cannula. In another embodiment of the invention, the main outer housing portion of the gas sealed access cap includes a compressible annular skirt adapted and configured to be releasably latched to the proximal bowl portion of the second robotic cannula. Alternatively, the proximal bowl portion of the second robotic cannula includes a movable compressible annular skirt adapted and configured to be releasably latched to the main outer housing portion of the gas sealed access cap.

In another embodiment of the invention, the main outer housing portion of the gas sealed access cap includes a spring biased hinged buckle adapted and configured to be releasably latched to the proximal bowl portion of the second robotic cannula. In another embodiment of the invention, the main outer housing portion of the gas sealed access cap includes a magnetic skirt adapted to be releasably secured to the proximal bowl portion of the second robotic cannula.

In one embodiment of the invention, the tri-lumen bullseye connector fitting is adapted and configured to communicate with a tri-lumen bullseye coupling that is associated with the distal end of the dual lumen portion of the tube set. In addition, a tri-lumen bullseye plug is provided for engagement with the tri-lumen bullseye coupling.

In an embodiment of the invention, the second robotic cannula has an elongated tubular body portion extending distally from the proximal bowl portion thereof, which includes a plurality of circumferentially spaced apart longitudinal beads on an interior surface thereof for accommodating gas flow around a surgical instrument extending through the tubular body portion. In another embodiment of the invention, the second robotic cannula has an elongated tubular body portion extending distally from the proximal bowl portion thereof, which includes a plurality of circumferentially spaced apart longitudinal channels in an interior surface thereof for accommodating gas flow around a surgical instrument extending through the tubular body portion. In yet another embodiment of the invention, the second robotic cannula has an elongated tubular body portion extending distally from the proximal bowl portion thereof, which includes a helical bead on an interior surface thereof for accommodating gas flow around a surgical instrument extending through the tubular body portion.

These and other features of the gas circulation system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas circulation system of the subject invention without undue experimentation, preferred embodiments thereof will be described in detail herein below with reference to the figures wherein:

FIG. 9 is a cross-sectional view taken along line 9-9 of FIG. 6, illustrating a distal end portion of the valve sealed access cap;

FIG. 10 is a cross-sectional view taken along line 10-10 of FIG. 6, illustrating a set of oval insufflation nares formed in the distal end portion of the valve sealed access cap;

FIG. 11 illustrates a set of triangular insufflation nares formed in the distal end portion of the valve sealed access cap;

FIG. 16 is a perspective view of the gas sealed access cap of the subject invention detachably engaged within the proximal housing of a robotic cannula;

FIG. 17 is a perspective view of the gas sealed access cap of the subject invention separated from the proximal housing of a robotic cannula;

FIG. 31 is a perspective view of the gas sealed access cap of the subject invention with a compressible skirt for detachably engaging the access cap to the proximal housing of a robotic cannula;

FIG. 32 is an exploded perspective view of the gas sealed access cap of FIG. 31 with parts separated for ease of illustration;

FIG. 33 is a cross-sectional view taken along line 33-33 of FIG. 31;

FIG. 34 is a cross-sectional view taken along line 34-34 of FIG. 31;

FIG. 35 is a top plan view of the gas sealed access port of FIG. 32, illustrating the way in which the compressible skirt is released from engagement with the proximal housing of the robotic cannula;

FIG. 41 is a perspective view of the gas sealed access cap of the subject invention with a magnetic skirt for detachably engaging the access cap to the proximal housing of a robotic cannula;

FIG. 42 is a cross-sectional view taken along line 42-42 of FIG. 41;

FIG. 43 is an exploded perspective view the gas sealed access cap of FIG. 41 with parts separated for ease of illustration;

DETAILED DESCRIPTION OF THE PREFERRED EMBODIMENTS

Figure 1:
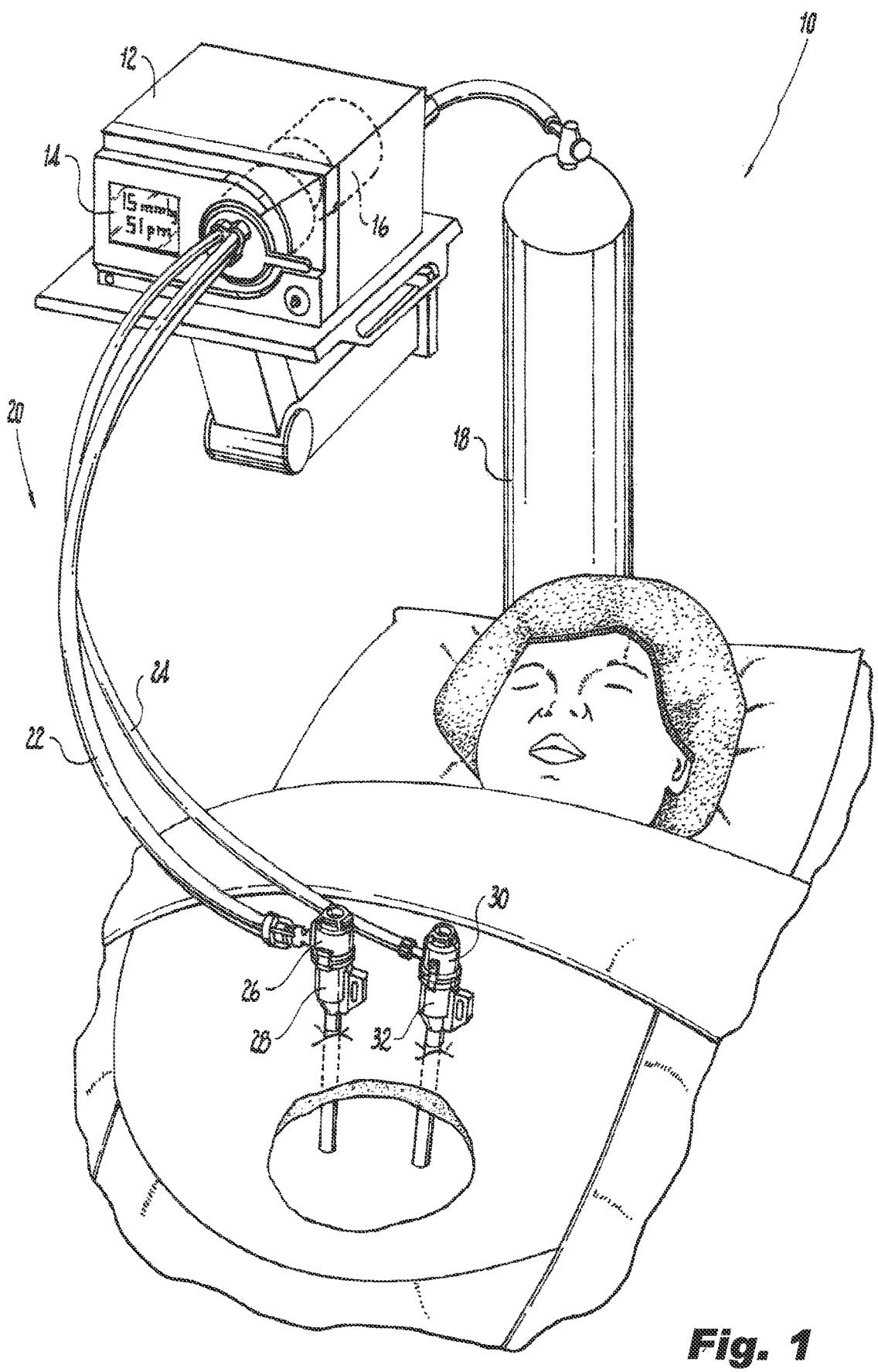
FIG. 1 is a perspective view of the gas circulation system of the subject invention in use during the performance of a robotically assisted laparoscopic surgical procedure, wherein the system includes a valve sealed access cap that is detachably engaged with a first robotic cannula, and a multi-lumen filtered tube set having a dual lumen portion connected to a gas sealed access cap that is detachably engaged with a second robotic cannula.

Referring now to the drawings wherein like reference numerals identify similar structural elements and features of the subject invention, there is illustrated in FIG. 1 a gas circulation system for performing an endoscopic surgical procedure in a surgical cavity of a patient, and more particularly, for performing a robotically assisted laparoscopic surgical procedure in the abdominal cavity of a patient that is constructed in accordance with a preferred embodiment of the subject disclosure and is designated generally by reference numeral 10.

The gas circulation system 10 of the subject invention is specifically designed to cooperate with a programmable multi-modal gas delivery system 12. The gas delivery system 12 is of the type described in commonly assigned U.S. Pat. No. 9,375,539, the disclosure of which is herein incorporated by reference in its entirety. The gas delivery system 12 includes a graphical user interface 14 for setting operating parameters and a pump 16 for facilitating the recirculation of pressurized gas relative to the surgical cavity of the patient. The gas delivery system 12 is connected to a source of surgical gas 18 for delivering insufflation gas to the surgical cavity of the patient.

In brief, the gas circulation system 10 includes a multi-lumen filtered tube set 20 having a dual lumen portion 22 and a single lumen portion 24. The single lumen portion 24 of tube set 20 is operatively connected to a valve sealed access cap 30 associated with a first robotic cannula 32. The dual lumen portion 22 of tube set 20 is operatively connected to a gas sealed access cap 26 associated with a second robotic cannula 28. Each of these components of the gas circulation system 10, and variations thereof, will be described in greater detail herein below.

Figure 2:
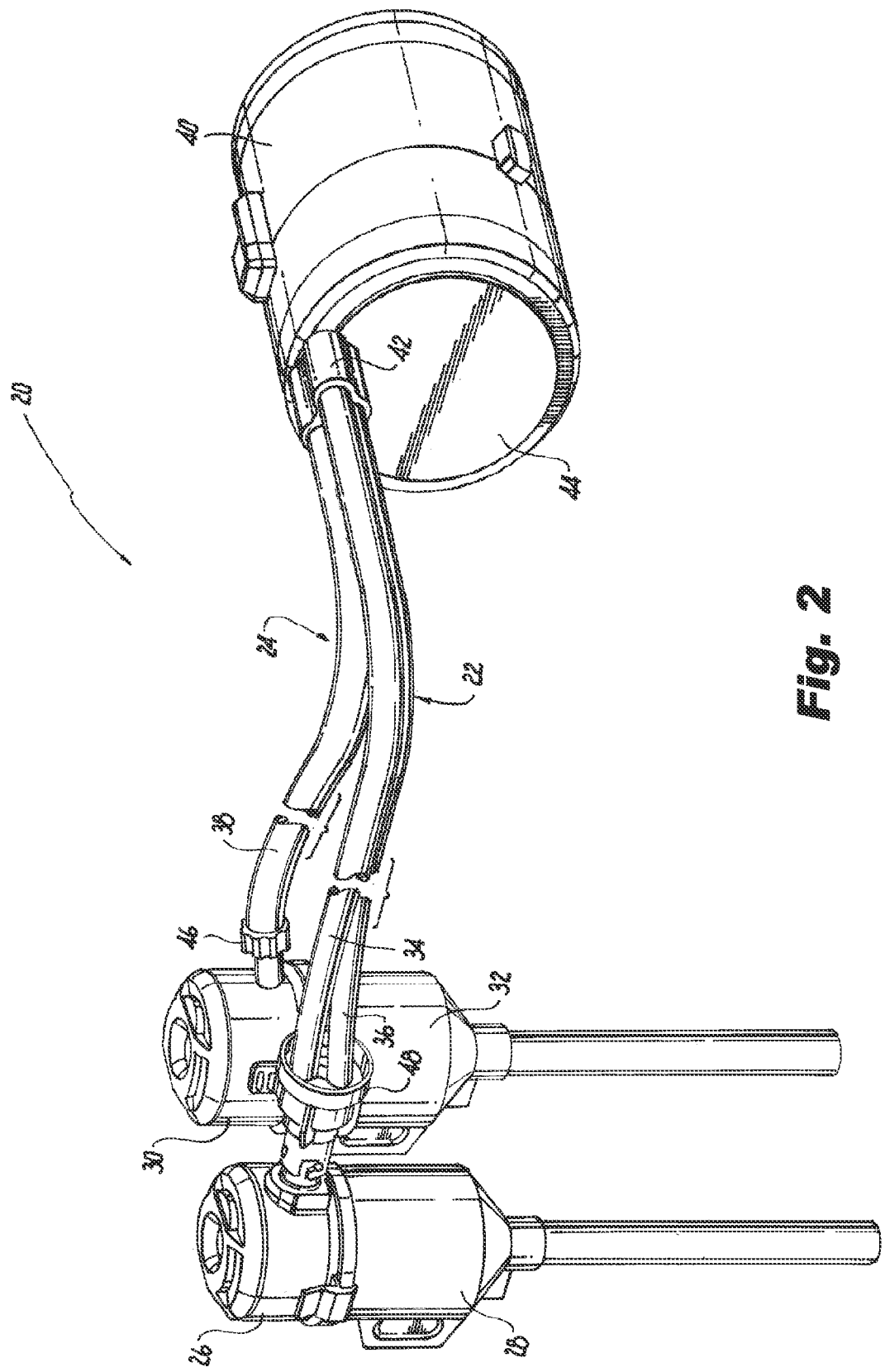
FIG. 2 is a perspective view of the multi-lumen filtered tube set shown in FIG. 1, together with the gas sealed access cap detachably engaged with the second robotic cannula and the valve sealed access cap detachably engaged with the first robotic cannula.
Figure 3:
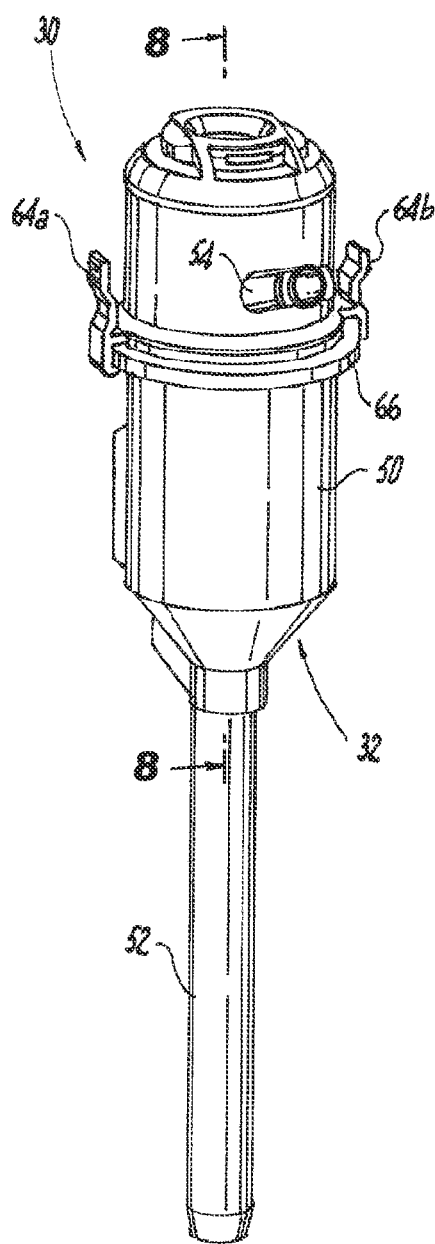
FIG. 3 is a perspective view of the valve sealed access cap of the subject invention detachably engaged within the proximal housing of a robotic cannula.
Figure 4:
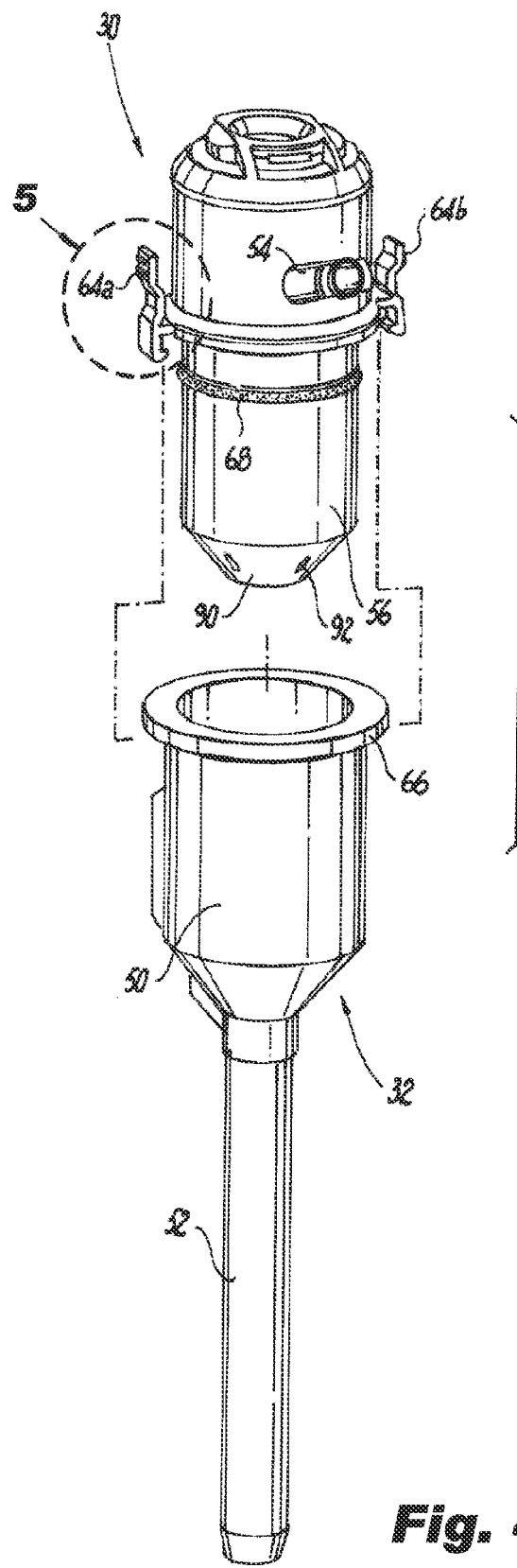
FIG. 4 is a perspective view of the valve sealed access cap of the subject invention separated from the proximal housing of a robotic cannula.

Referring to FIG. 2, the dual lumen portion 22 of tube set 20 has a pressurized gas line 34 and a return gas line 36 for facilitating gas recirculation relative to the surgical cavity of the patient and for facilitating the evacuation of smoke filled gas from the surgical cavity resulting from electro-cauterization tasks or the like. The single lumen portion 24 of tube set 20 defines a gas supply and sensing line 38 that has two distinct functions. It facilitates the delivery of insufflation gas to the surgical cavity of the patient and it also facilitates the periodic sensing of pressure within the surgical cavity of the patient.

The tube set 20 is operatively associated with a multi-path filter cartridge assembly 40. More particularly, the gas lines of the tube set 20 extend from a fitting 42 on the end cap 44 of the filter cartridge assembly 40. A filter cartridge assembly of this type is disclosed for example in commonly assigned U.S. Pat. No. 9,067,030, the disclosure of which is herein incorporated by reference in its entirety. The filter cartridge assembly 40 is preferably designed for a single use and is thereafter disposable. It is specifically designed to cooperate with the multi-modal gas delivery system 12, illustrated in FIG. 1.

While not shown here, the filter cartridge assembly 40 includes a first filtered flow passage communicating with the pressurized gas line 34 of the dual lumen portion 22 of the tube set 20, a second filtered flow passage communicating with the return gas line 36 of the dual lumen portion 22 of the tube set 20, and a third filtered flow passage communicating with the gas supply and sensing line 38 of the single lumen portion 24 of the tube set 20.

As shown in FIG. 2, the single lumen portion 24 of the tube set 20 includes an enlarged luer type connector fitting 46 for coupling with the valve sealed access cap 30. The enlarged luer type connector fitting 46 will be discussed in greater detail below with reference to FIGS. 7 and 8. The dual lumen portion 22 of the tube set 20 includes a multi-lumen connector fitting 48 for coupling with the gas sealed access cap portion 26. As described in more detail below, the subject invention describes several different embodiments of a multi-lumen connector fitting 48 for the dual lumen portion 22 of tube set 20.

Referring now to FIGS. 3 through 8, the valve sealed access cap 30 of gas circulation system 10 is adapted and configured for cooperative reception within a proximal bowl portion 50 of the robotic cannula 32, which further includes an elongated tubular body portion 52. The valve sealed access cap 30 has an inlet path 54 for communicating with the gas supply and sensing line 38 of the tube set 20. More particularly, as explained in more detail below, the inlet path 54 is a luer type connector that cooperates with the luer type connector fitting 46 on the distal end of the gas supply and sensing line 38.

Figure 6:
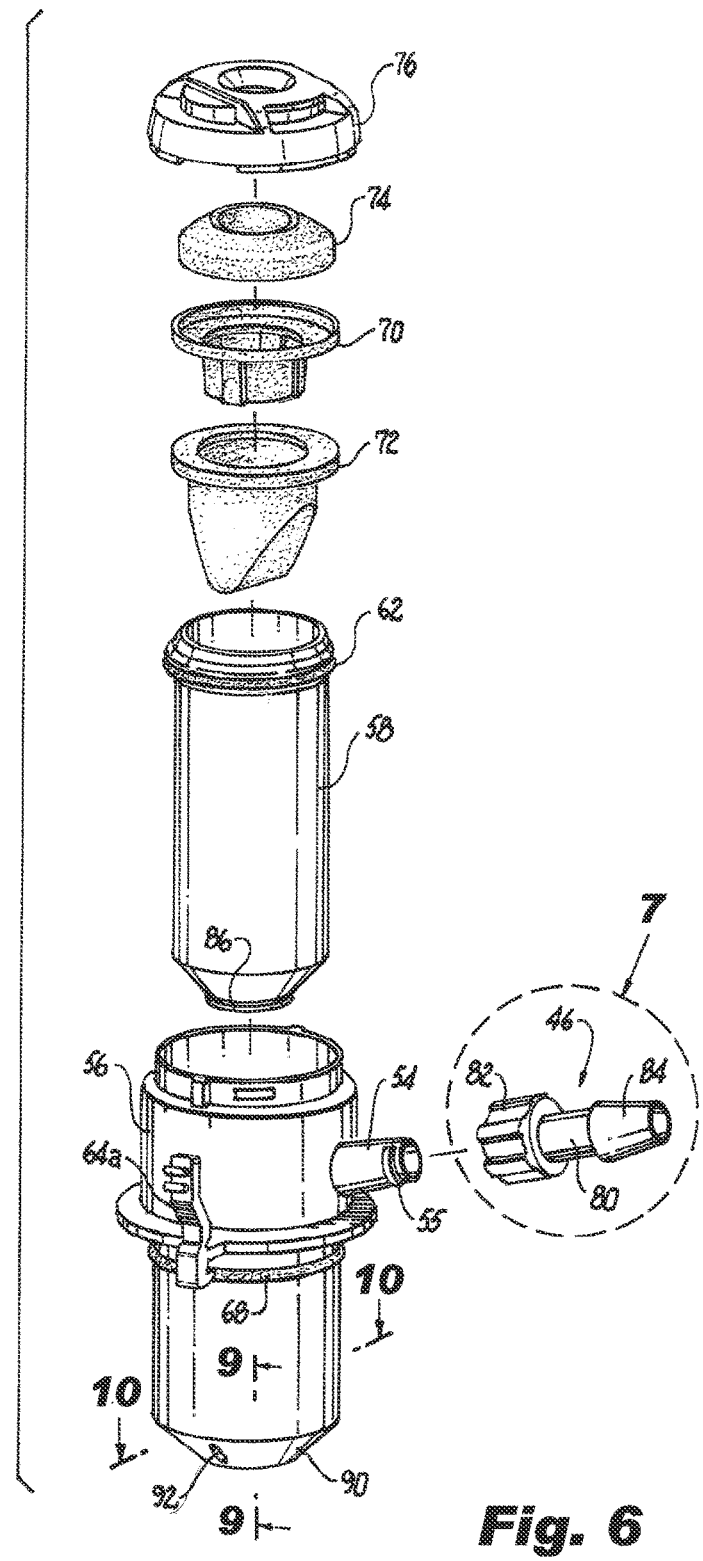
FIG. 6 is an exploded perspective view of the valve sealed access cap of the subject invention, with parts separated for ease of illustration.
Figure 8:
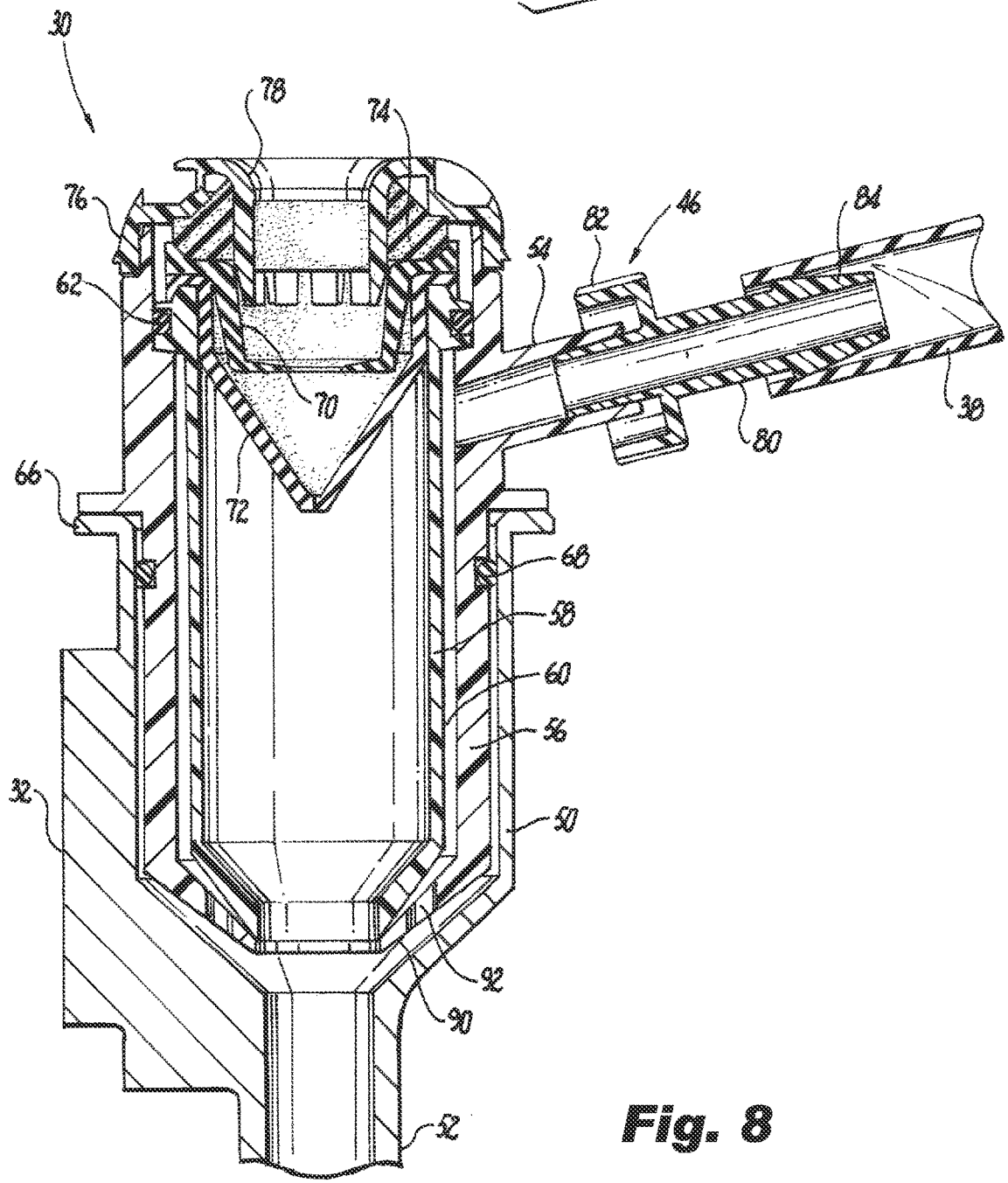
FIG. 8 is cross-sectional view taken along line 8-8 of FIG. 3, with the luer connector attached to the luer fitting of the valve sealed access cap.

As best seen in FIGS. 6 and 8, the valve sealed access cap 30 includes an elongated generally cylindrical outer housing portion 56 and an elongated generally cylindrical inner body portion 58 that is dimensioned and configured to nest within the outer housing portion 56. An annular flow channel 60 is advantageously formed between the outer housing portion 56 and the inner body portion 58 in communication with the inlet path 54. An inner O-ring 62 seals the annular channel 60 between the outer housing portion 56 and the inner body portion 58 to provide frictional engagement and prevent gas leakage therebetween.

Figure 5:
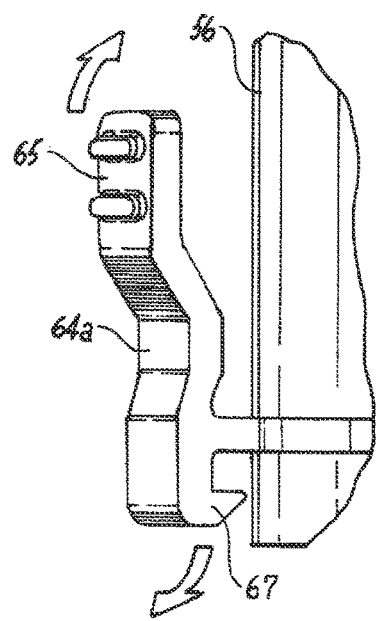
FIG. 5 is an enlarged localized perspective view taken from FIG. 4 of one of the diametrically opposed flexible clips associated with the valve sealed access cap for releasably latching to a flange of the proximal housing of the robotic cannula.

The outer housing portion 56 of valve sealed access cap 30 includes a pair of diametrically opposed flexible clips 64a, 64b that are adapted and configured to be releasably latched to an upper annular flange 66 of the proximal bowl portion 50 of robotic cannula 32. As best seen in FIG. 5, by way of example, the flexible clip 64a includes an upper portion 65 that can be readily flexed inwardly to release a lower clip portion 67. The opposed flexible clip 64b is similarly constructed. An outer O-ring 68 surrounds the periphery of the outer housing portion 56 so that it is positioned between the outer housing portion 56 and the interior wall of the proximal bowl portion 50 of robotic cannula 32 to provide frictional engagement and prevent gas leakage therebetween.

The inner body portion 58 of the valve sealed access cap 30 supports a primary valve 70 and a secondary valve 72. Preferably, the primary valve 70 is a circular septum valve and the secondary valve 72 is a duckbill valve. Other types of mechanical valve seals known in the art can be used as well. The primary valve 70 is nested in and located proximal to the secondary valve 72. A sound attenuating disc 74 made of a foam material is positioned within the valve sealed access cap 30 proximal to the primary valve 70 for reducing sound levels and to aid in holding the primary valve 70 and secondary valve 72 in place during instrument insertion, removal and manipulation.

A lid 76 is engaged with a proximal end of the outer housing portion 56 to secure the inner body portion 58 within the outer housing portion 56 and to provide security during instrument insertion, removal and manipulation. The lid 76 defines the entryway or inlet port 78 of the access cap 30, through which surgical instruments and the like are introduced into the cannula 32. The lid 76 may be mechanically attached to the outer housing portion 56 by clips or tabs or it may be heat welded, spin welded or glued in place. The lid 76 further secures the inner body portion 58, the sound attenuating disc 74, the primary valve 70 and the secondary valve 72 within the outer housing portion 56 relative to the inner body portion 58.

Figure 7:
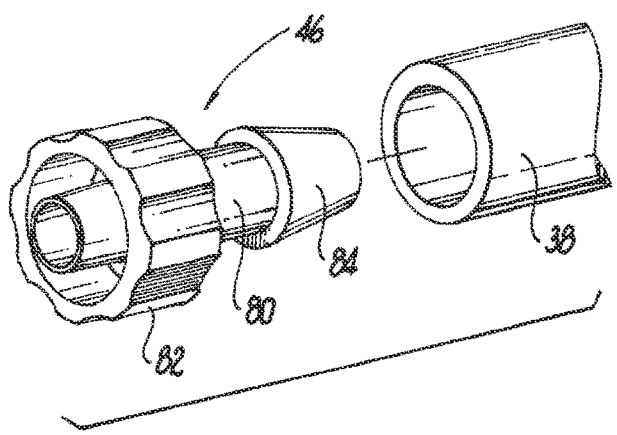
FIG. 7 is an enlarged localized perspective view taken from FIG. 6 of the luer connector for connecting the valve sealed access cap to the single lumen of the filtered tube set.

Referring now to FIGS. 7 and 8, preferably, the inlet path 54 that is integrally formed with the outer housing portion 56 of access cap 30 is a luer type connector. Thus, it has a thread form 55 that is configured to mate with the luer type connector fitting 46 (See FIG. 6). The luer type fitting 46 has an elongated stem 80 with a proximal skirt 82 and a barbed distal tip 84. The proximal skirt 82 mates with the thread form 55 of inlet path 54, and the distal tip 84 mates with the insufflation and sensing line 38 of the tube set 20. The luer type fitting 46 and the inlet path connector 54 are selectively sized to achieve a desired amount of gas flow into the inlet path 54. Thus, a person of ordinary skill will readily appreciate that the dimensions or size of these features of the gas circulation system 10 are larger than standard luer type connective fittings that are known and used in the art. This advantageously eliminates a choke point in the flow path of the access cap 30 and maximizes the mass flow rate therethrough for a given driving pressure.

As best seen in FIGS. 8 and 9, an inwardly tapered distal end surface 86 of the inner body portion 58 of access cap 30 compressively and intimately engages against an interior distal surface 88 of an inwardly tapered distal wall 90 of the outer housing portion 56 of access cap 30 to enclose the annular gas flow channel 60 in a gas-tight manner.

Figure 12:
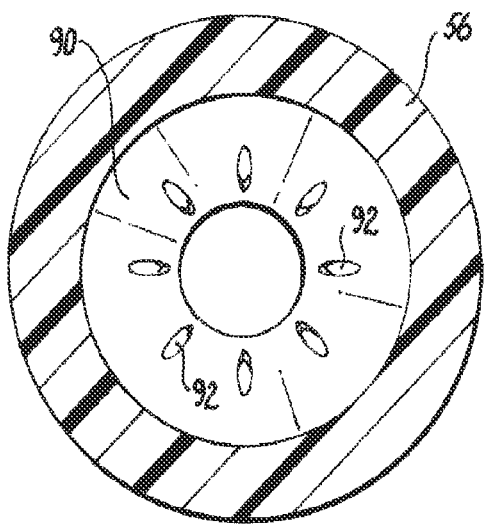
FIG. 12 illustrates another set of oval insufflation nares formed in the distal end portion of the valve sealed access cap.

In one embodiment of the invention, the annular channel 60 communicates with the proximal bowl portion 50 of the robotic cannula 32 through a plurality of circumferentially spaced apart nares or openings 92 that are formed in the inwardly tapered distal wall 90 of the outer housing portion 56. Here, as shown in FIGS. 10 and 12, the plurality of nares 92 are oval shaped and extend radially outwardly from a central axis of the outer housing portion 56. Those skilled in the art will readily appreciate that the number, shape and/or size of the nares can be selected to provide a desired gas flow.

Figure 13:
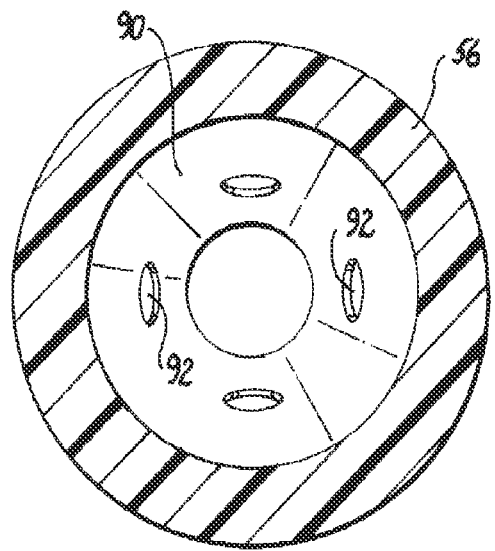
FIG. 13 illustrates yet another set of oval insufflation nares formed in the distal end portion of the valve sealed access cap.
Figure 14:
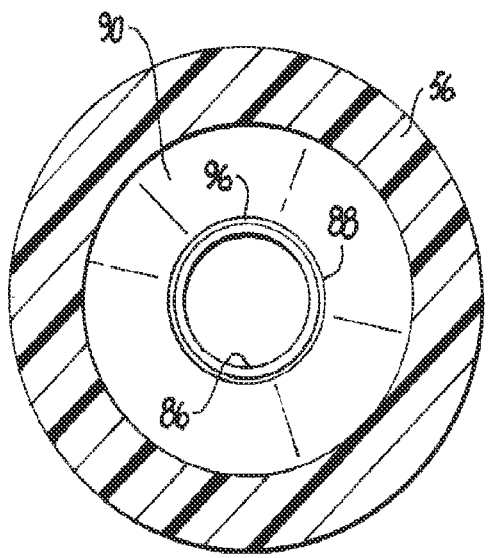
FIG. 14 illustrates an annular insufflation gap formed in the distal end portion of the valve sealed access cap.

Alternatively, as shown in FIG. 13, the plurality of oval nares 92 can extend generally tangentially relative to a central axis of the outer housing portion. As shown in FIG. 11, a plurality of triangular shaped nares 94 can be provided, which would extend radially outwardly from a central axis of the outer housing portion 56. In another embodiment of the invention shown in FIG. 14, the annular channel 60 communicates with the proximal bowl portion 50 of robotic cannula 32 through an annular nare 96 that is defined between an inwardly tapered distal wall 86 of the inner body portion 58 and the inwardly tapered distal wall 88 of the outer housing portion 56.

Figure 15:
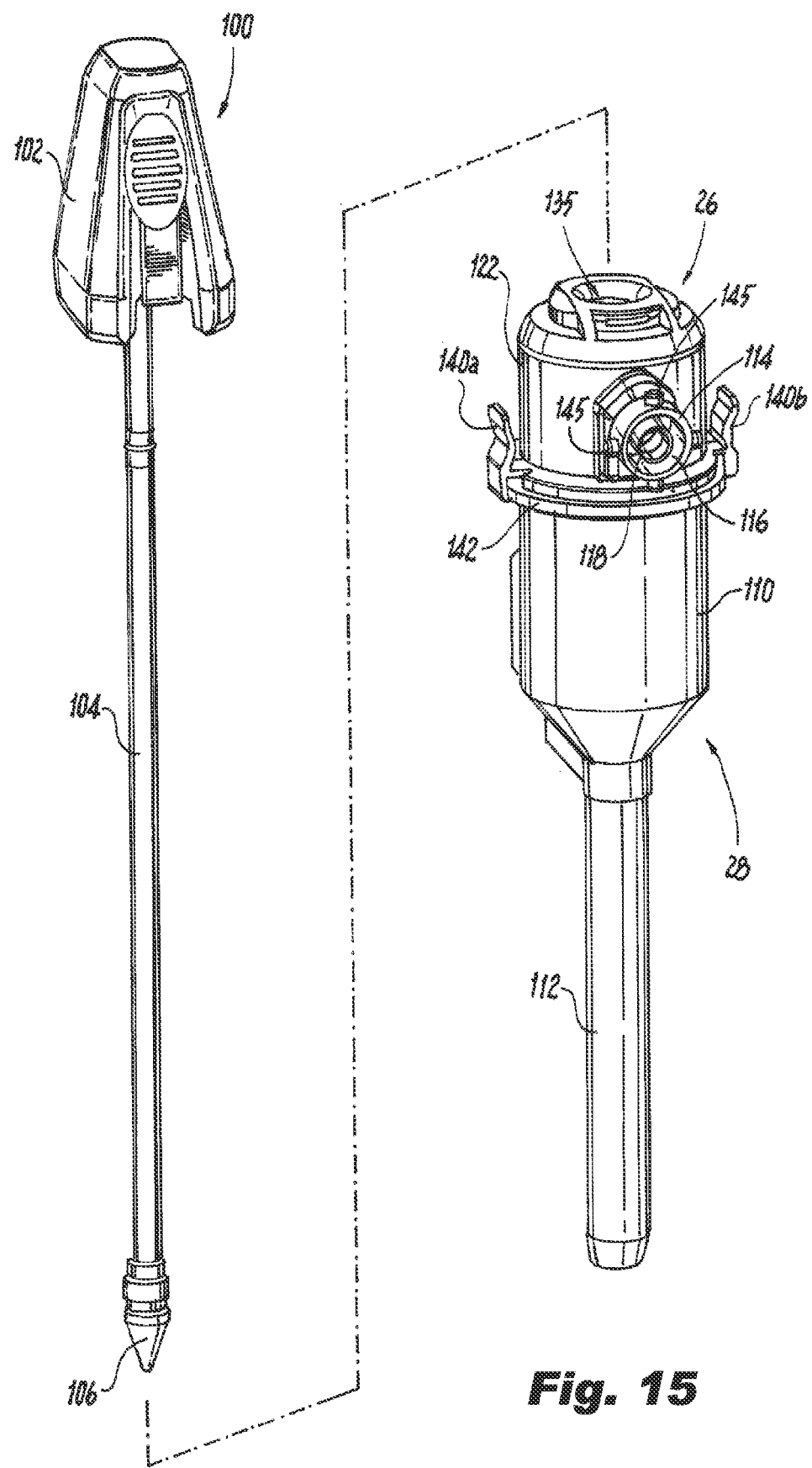
FIG. 15 is a perspective view of the gas sealed access cap of the subject invention engaged within a robotic cannula, along with an obturator for gaining initial access to the abdominal cavity of a patient.

Referring now to FIGS. 15 through 19, the gas sealed access cap 26 of gas circulation system 10 is adapted and configured for cooperative reception within the proximal bowl portion 110 of robotic cannula 28, which further includes an elongated tubular body portion 112. As illustrated in FIG. 15, the gas sealed access cap 26 is adapted and configured to cooperate with an obturator 100 for gaining initial access to the abdominal cavity of a patient. The obturator 100 includes a proximal handle portion 102 for cooperatively engaging the access cap 26, an elongated tubular shaft 104 dimensioned to extend through the robotic cannula 28 and a sharpened cutting tip 106 for piercing through the abdominal wall. Those skilled in the art will readily appreciate that the obturator 100 can also be employed with the valve sealed access cap 30 and robotic cannula 32 described above.

The gas sealed access cap 26 has a multi-lumen connector 114 for communicating with the multi-lumen connector 48 associated with the dual lumen portion 22 of tube set 20. In this embodiment of the invention, the multi-lumen connector 114 is a bi-lumen bullseye connector, which includes a radially outer gas inlet lumen 116 and a central gas outlet lumen 118. The gas inlet lumen 116 of connector 114 communicates with the pressurized gas line 34 of the dual lumen portion 22 of the tube set 20, and the gas outlet lumen 118 of connector 114 communicates with the return gas line 36 of the dual lumen portion 22 of the tube set 20. The bi-lumen connector 114 extends to a mounting manifold 120 and it includes a plurality of circumferentially spaced apart radially outwardly extending lugs or posts 145 for interacting with the multi-lumen connector fitting 48, as described in more detail below.

Figure 18:
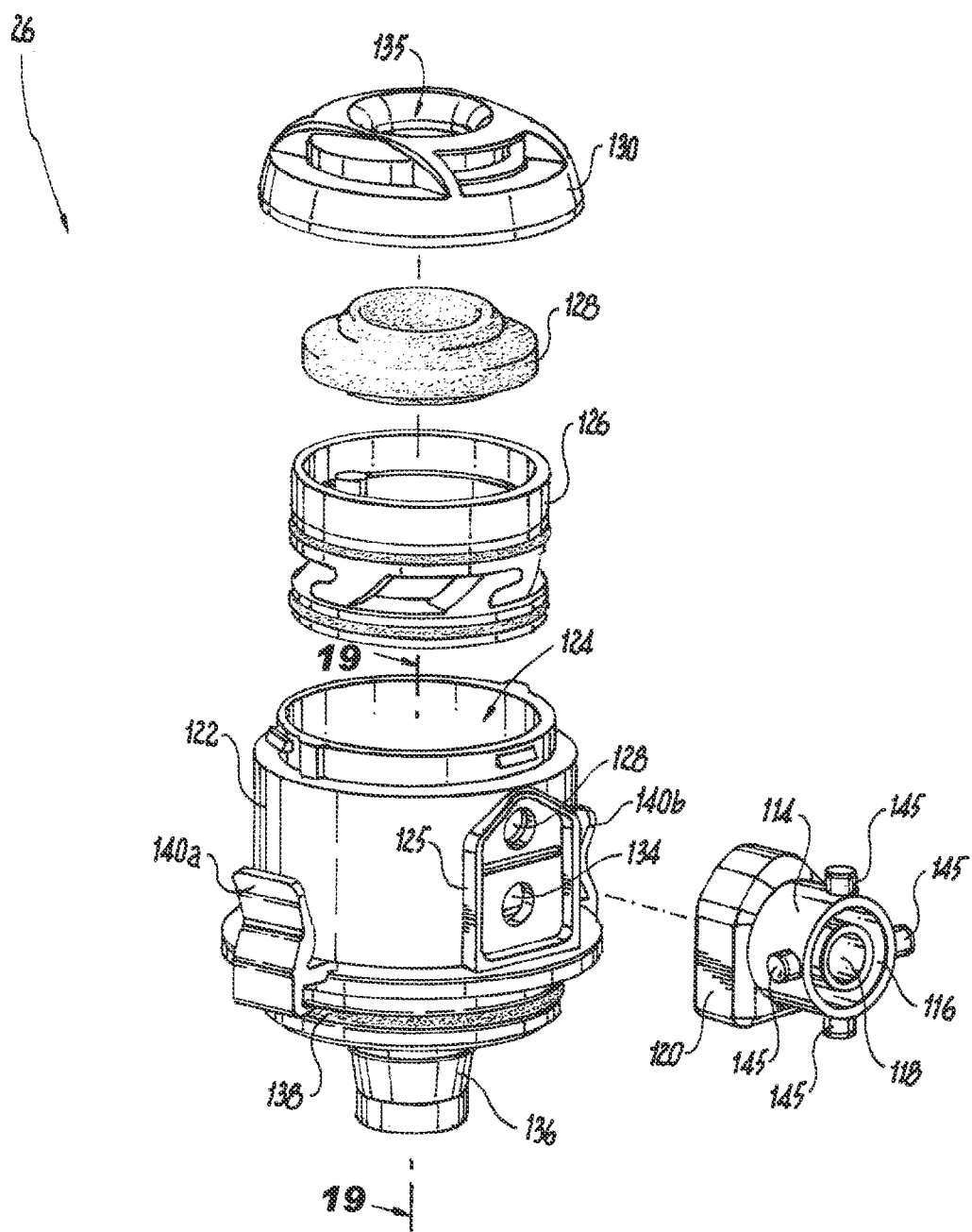
FIG. 18 is an exploded perspective view of the gas sealed access cap of the subject invention, with parts separated for ease of illustration.

Referring to FIG. 18, the gas sealed access cap 28 includes a main housing portion 122 defining an interior cavity 124 that supports a two-piece annular jet assembly 126 for receiving pressurized gas from an inlet port 128 communicating with gas inlet lumen 116 of connector 114. The annular jet assembly 126 is adapted and configured to generate a gaseous sealing zone within the robotic cannula 28 to maintain a stable pressure within the surgical cavity of the patient. The structure and function of the jet assembly 126 is described in detail in commonly assigned U.S. Pat. No. 8,795,223, the disclosure of which is herein incorporated by reference in its entirety.

The main housing portion 122 of access cap 28 includes a mounting flange 125 for cooperatively receiving the manifold 120 of the multi-lumen connector 114. A sound attenuating disc 128 made of foam material is positioned within the main housing portion 122 of the gas sealed access cap 26 proximal to the annular jet assembly 126 for reducing sound levels generated by the pressurized gas streaming through the jet assembly 126. A lid 130 is engaged with a proximal end of the outer housing portion 122 to secure the annular jet assembly 126 and sound attenuating disc 128 within the main housing portion 122. The lid 130 defines the main entry port 135 for the gas sealed access cap 26 through which surgical instruments and the like are introduced into the robotic cannula 28.

Figure 19:
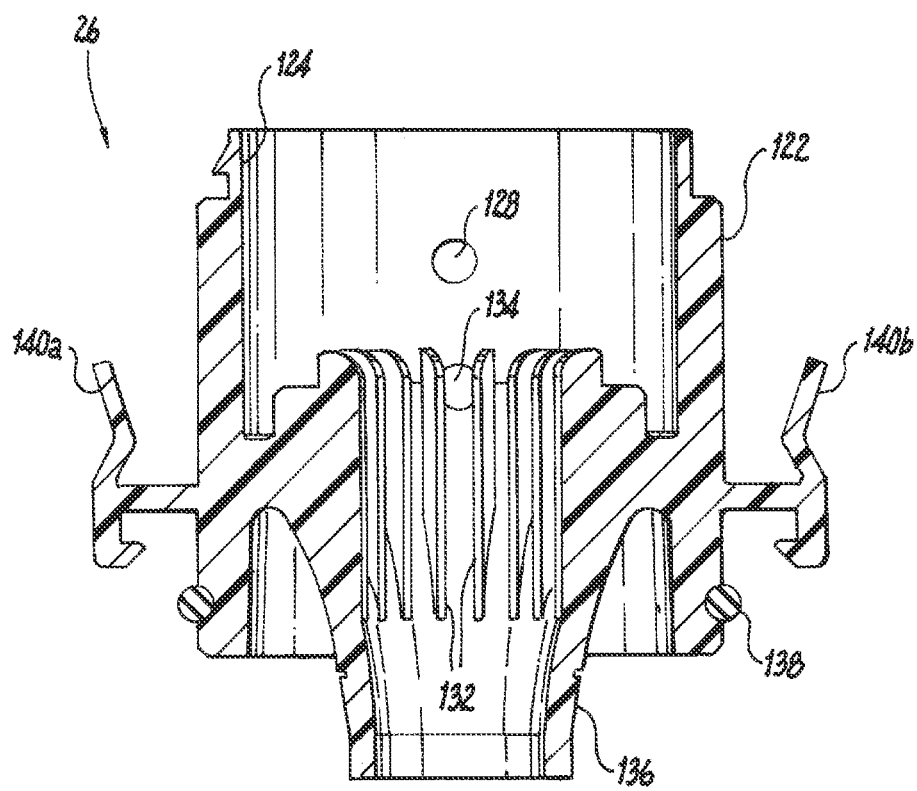
FIG. 19 is a cross-sectional view taken along line 19-19 of FIG. 18, illustrating the integrally formed interior structures of the housing of the gas sealed access cap.

In addition, as best seen in FIG. 19, the main housing portion 122 of the gas sealed access cap 26 includes an integrally formed body of circumferentially spaced apart vanes 132 for directing spent gas from the gaseous sealing zone to the outlet lumen 118 of connector 114 by way of an outlet port 134 in the main housing portion 122 of the gas sealed access cap 26. This spent gas is withdrawn from the area by the recirculation flow generated by the pump 16 in the multi-modal gas delivery system 12 shown in FIG. 1. Under certain circumstances, the spent gas may include smoke filled gas generated in the surgical cavity.

The body of integrally formed circumferentially spaced apart vanes 132 surround the inner periphery of the interior cavity 124 of the main housing portion 122 and they extend distally to an inwardly tapered integral tubular extension 136, which extends distally into the proximal bowl portion 110 of robotic cannula 28. Similar guide vanes are described in commonly assigned U.S. Pat. No. 8,795,223, but they are not formed integral with a housing.

An outer O-ring 138 surrounds a lower section of the main housing portion 122 so that it is positioned between the main housing portion 122 of the gas sealed access cap 26 and the proximal bowl portion 110 of robotic cannula 28 to form an air-tight seal therebetween. The main housing portion 122 of gas sealed access cap 26 also includes a pair of diametrically opposed flexible clips 140a, 140b that are adapted and configured to be releasably latched to an upper annular flange 142 of the proximal bowl portion 110 of robotic cannula 28, as illustrated for example in FIGS. 15 and 16.

Figure 20:
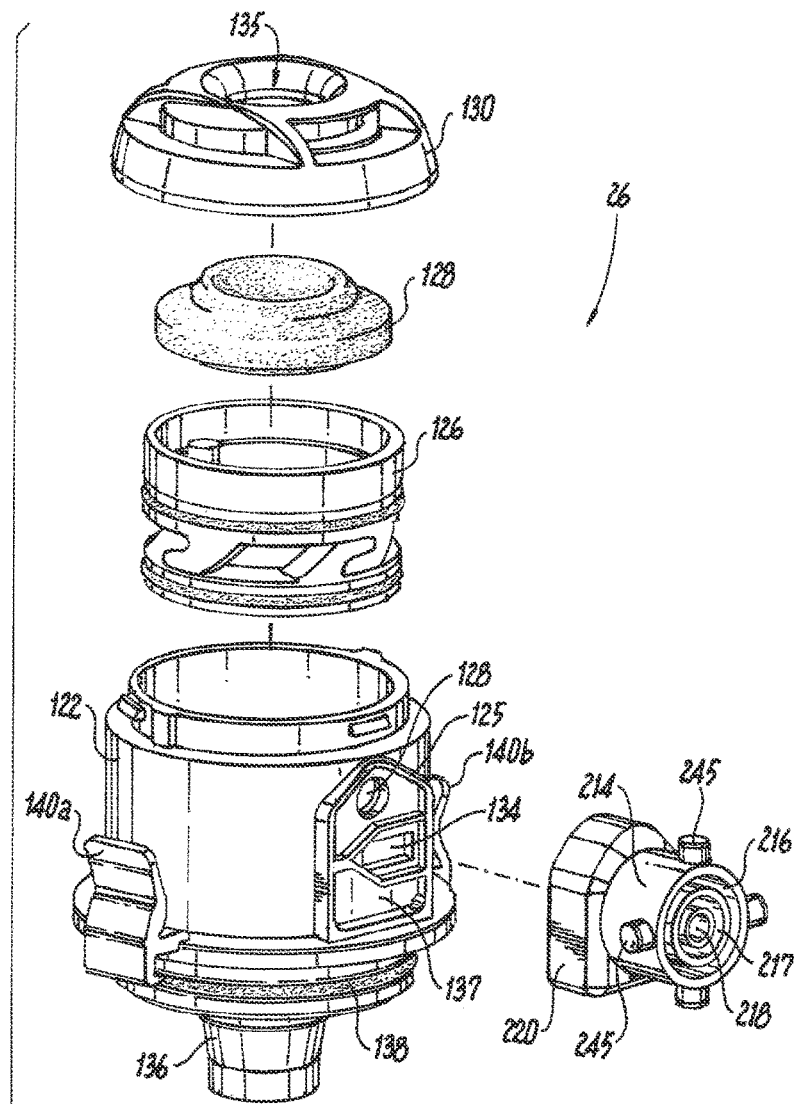
FIG. 20 is an exploded perspective view of another embodiment of the gas sealed access cap of the subject invention, with parts separated for ease of illustration.
Figure 21:
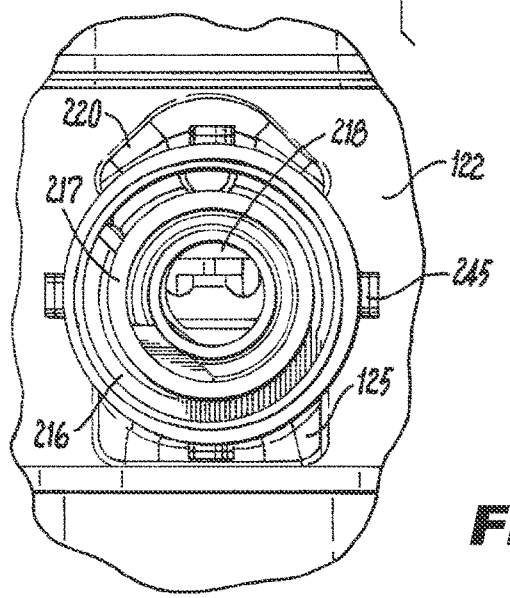
FIG. 21 is an enlarged plan view of the bulls-eye connector of the gas sealed access cap of FIG. 20.
Figure 22:
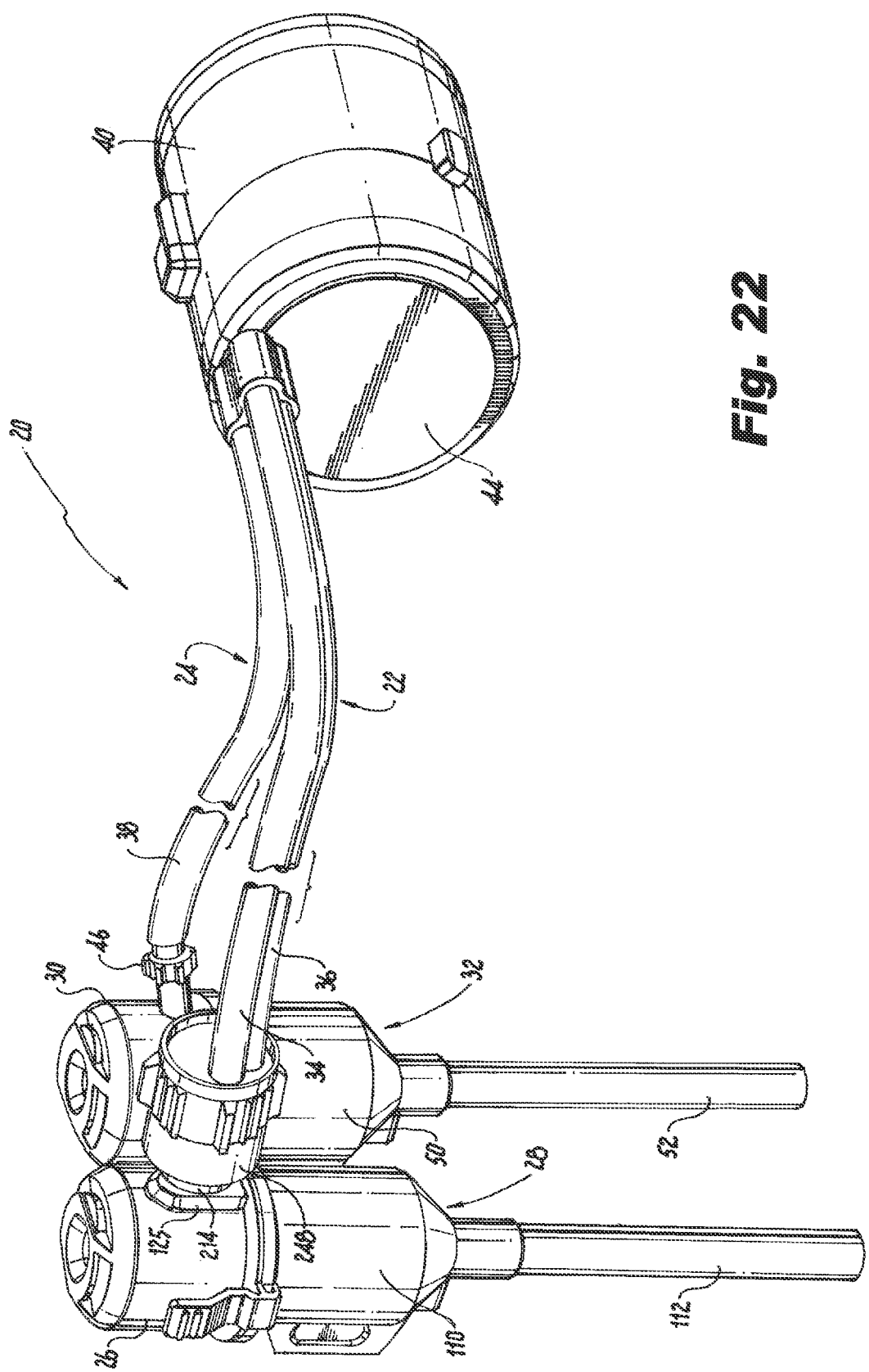
FIG. 22 is a perspective view of the multi-lumen filtered tube set of the subject invention, wherein the dual lumen portion of the tube set has tri-lumen connector for coupling with the gas sealed access cap of the subject invention.
Figure 23:
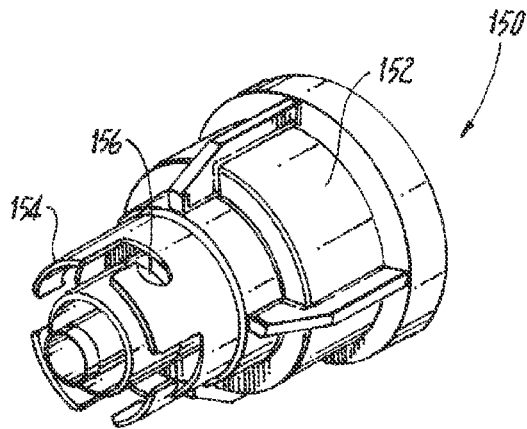
FIG. 23 is a perspective view of a bi-lumen connector for coupling with the gas sealed access cap of the subject invention, which includes a bayonet-type coupling feature.
Figure 24:
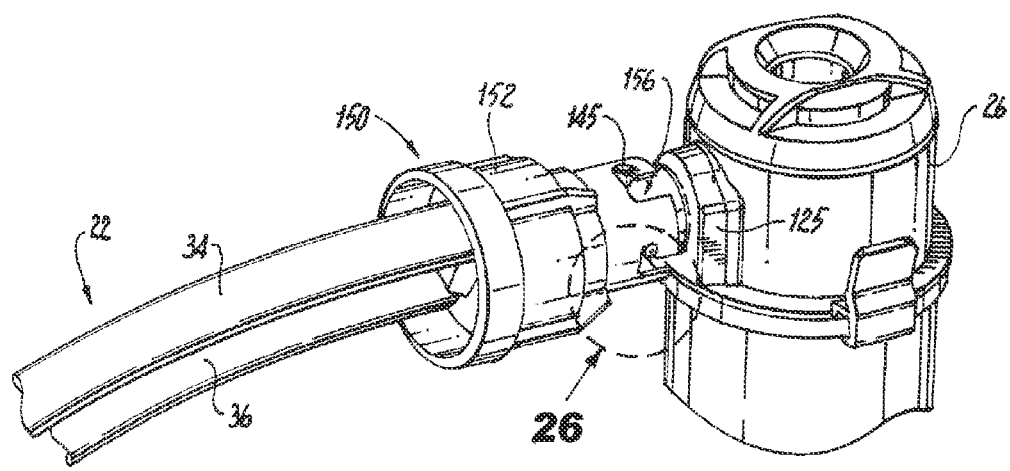
FIG. 24 is a perspective view of the bi-lumen connector of FIG. 23 associated with the dual lumen portion of the filtered tube set of the subject invention, and coupled to the dual lumen fitting of the gas sealed access cap of the subject invention.

Referring now to FIGS. 20 through 22, in another embodiment of the subject invention, the multi-lumen connector of the gas sealed access port 26 is a tri-lumen bullseye connector, which is designated generally by reference numeral 214. A tri-lumen connector of this type is disclosed in commonly assigned U.S. Pat. No. 9,526,886, the disclosure of which is herein incorporated by reference in its entirety. This feature is currently employed on commercially available AirSeal access port products that are manufactured and sold by SurgiQuest, Inc., a wholly owned subsidiary of ConMed Corporation, so it is a readily available component. For this reason, it can be easily adapted for use with the gas sealed access cap 26, thus reducing the manufacturing costs and time to market for this new access device.

More particularly, as illustrated in FIGS. 20 and 21, the tri-lumen bullseye connector 214 for access cap 26 includes an outer lumen 216 for receiving gas from a pressurized gas line 34, a central lumen 218 for discharging spent gas to the gas return line 36, and an intermediate lumen 217 therebetween. In this case, the intermediate lumen 217 is not connected to any gas line of the tube set 20, and the inlet area 137 that is located within the bounds of mounting flange 125 is blocked or otherwise blank, thus rendering the intermediate lumen 217 moot. It is essentially a vestigial or unused feature of the connector 214. Consequently, the tri-lumen bullseye fitting 248 that is shown in FIG. 22 is only associated with the dual lumen portion 22 of tube set 20 (i.e., lumens 34 and 36), even though the fitting 248 is adapted and configured to mate with the tri-lumen connector 214.

Turning now to FIGS. 23 through 26, there is illustrated another embodiment of a bullseye connector fitting for rotatably coupling with the connector 114 of the gas sealed access cap 26 of the subject invention, which is designated generally by reference numeral 150. The bullseye connector fitting 150 includes a proximal portion 152 for receiving the dual lumen portion 22 of the tube set 20 and a distal portion 154 for engaging with the spaced apart lugs or posts 145 on the connector 114. The distal portion 154 of connector fitting 150 includes a set of generally J-shaped slots 156 for receiving the lugs 145.

Figure 25:
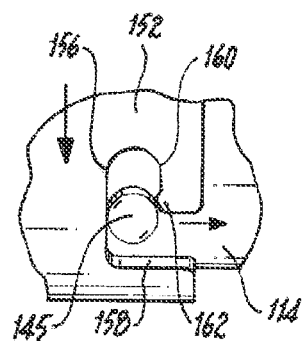
FIGS. 25 and 26 are enlarged localized views taken from FIG. 24 showing the engagement of a bayonet channel of the bi-lumen connector with a lug on the fitting of the gas sealed access cap.
Figure 26:
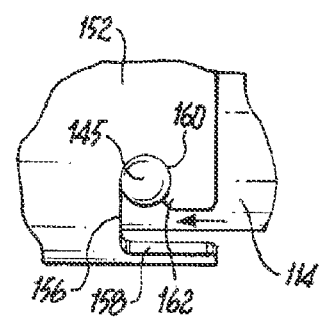
Figure 27:
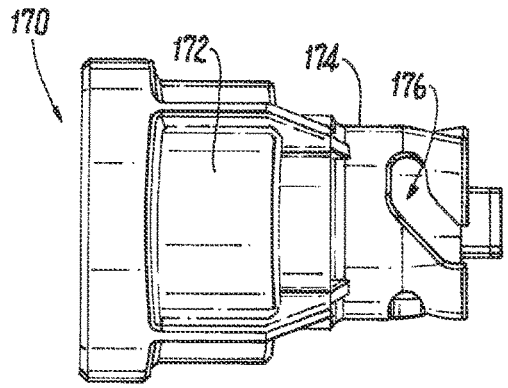
FIG. 27 is a perspective view of another bi-lumen connector for coupling with the gas sealed access cap of the subject invention, which includes another bayonet-type coupling feature.
Figure 28:
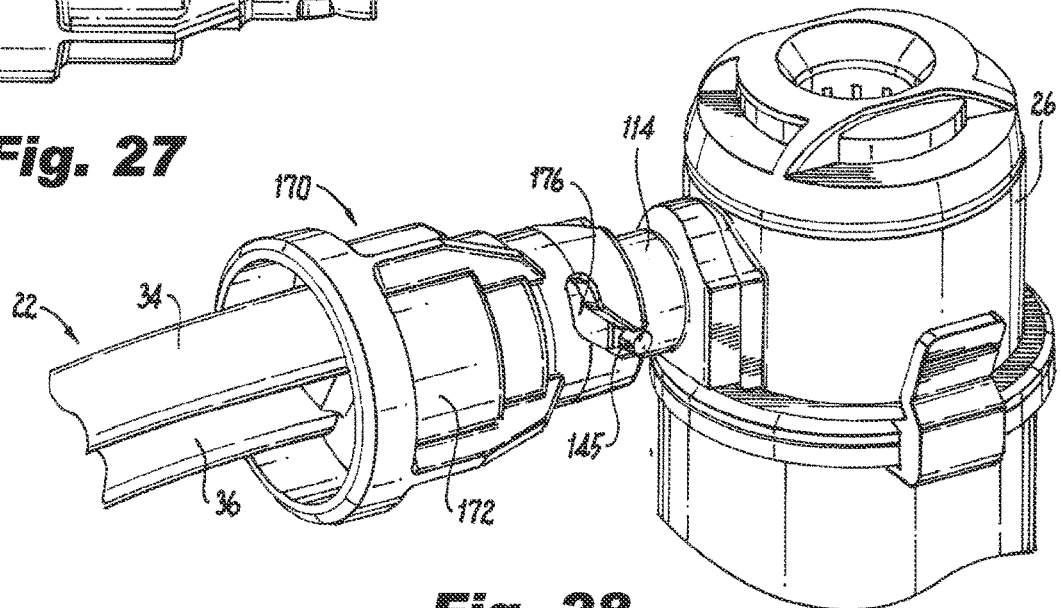
FIG. 28 is a perspective view of the bi-lumen connector of FIG. 27 associated with the dual lumen portion of the filtered tube set of the subject invention, and coupled to the dual lumen fitting of the gas sealed access cap of the subject invention.

As best seen in FIGS. 25 and 26, each J-shaped slot 156 has a leading leg section 158 and a trailing foot section 160. An enlarged bulb 162 is formed at the entryway to the trailing foot section 158 of slot 156 that must be overcome by rotational force during coupling so that the lug 145 can be locked in place. Those skilled in the art will readily appreciate that the coupling feature shown in FIGS. 23 through 26 can be employed with a bi-lumen connector fitting or a tri-lumen connector fitting in accordance with the subject invention.

Referring to FIGS. 27 through 30, there is illustrated another embodiment of a bullseye connector fitting for rotatably coupling with the connector 114 of the gas sealed access cap 26 of the subject invention, which is designated generally by reference numeral 170. The connector fitting 170 includes a proximal portion 172 for receiving the dual lumen portion 22 of the tube set 20 and a distal portion 174 for engaging with the spaced apart lugs or posts 145 on the connector 114.

Figure 29:
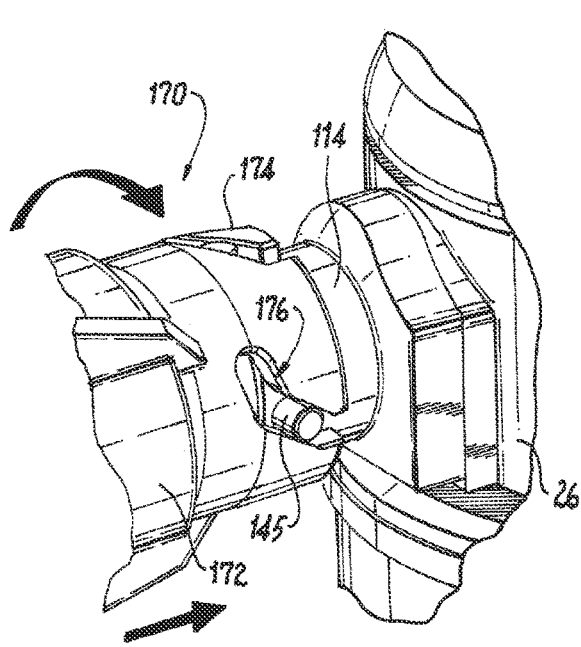
FIGS. 29 and 30 are enlarged localized views showing the engagement of a bayonet channel of the bi-lumen connector of FIG. 27 with a lug on the fitting of the gas sealed access cap as shown in FIG. 28.
Figure 30:
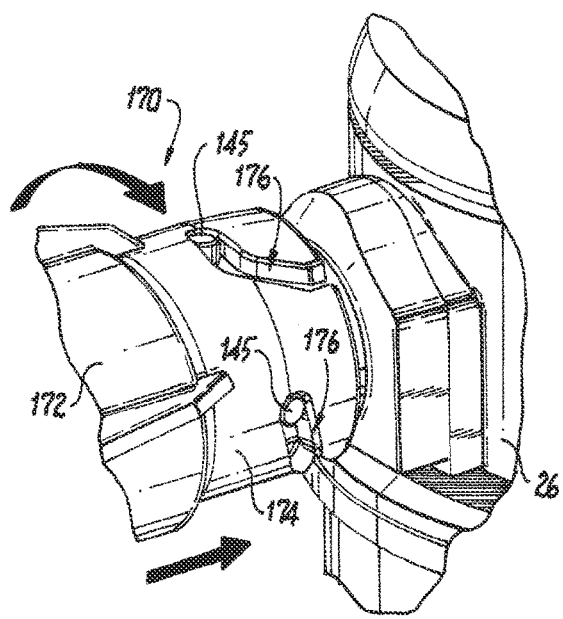

The distal portion 174 of connector fitting 170 includes a set of circumferentially spaced apart generally hockey stick shaped slots 176 defining a corkscrew type coupling feature for receiving the lugs 145 and for frictionally retaining the lugs 145 in a locked position within the slots 176 upon clockwise rotation of the fitting 170 relative to the connector 114, as best seen in FIGS. 29 and 30. Those skilled in the art will readily appreciate that the coupling feature shown in FIGS. 27 through 30 can be employed with a bi-lumen connector fitting or a tri-lumen connector fitting in accordance with the subject invention.

Referring to FIGS. 31 through 36, there is illustrated an attachment mechanism for releasably attaching an embodiment of the gas sealed access cap 26 to the proximal bowl portion 110 of robotic cannula 28, instead of the diametrically opposed flexible clips 140a, 140b previously described herein and shown in FIGS. 16 and 17. More particularly, FIGS. 31 through 36 illustrate an oval shaped compressible pinch skirt 220 that is integral with and surrounds the lower section of the main housing portion 122 of the gas sealed access cap 26.

The compressible pinch skirt 220 has two diametrically opposed compression tabs 222a, 222b and two diametrically opposed clip ledges 223a, 223b with windows 227a, 227b for moldability. The compression tabs 222a, 222b are adapted and configured to enable the application of a manual force to the skirt 220 in a radially inward direction, as shown in FIG. 35. This causes the skirt 220 to expand radially outwardly along an axis that is generally transverse to the force vectors, so that the clip ledges 223a, 223b can be physically released from below the proximal flange 142 of the bowl portion 110 of access cap 26. Diametrically opposed C-shaped cutouts 229a, 229b are formed in the pinch skirt 220 adjacent the compression tabs 222a, 222b, respectively, to allow for more displacement of the clip ledges 223a, 223b and to reduce the overall rigidity of the pinch skirt 220.

As best seen in FIG. 33, a compressible ring 226 is positioned underneath the pinch skirt 220 so that it sits between pinch skirt 220 and the proximal flange 142 of the bowl portion 110, to provide a seal and a resilient biasing force therebetween, enhancing the security of the pinch skirt 220. It is envisioned that the gasket 226 can be an over-molded elastomer, a flat O-ring or a foam material. Those skilled in the art will readily appreciate that the attachment feature shown in FIGS. 31 through 36 can be employed with the valve sealed access cap 30 in accordance with the subject invention.

Figure 39:
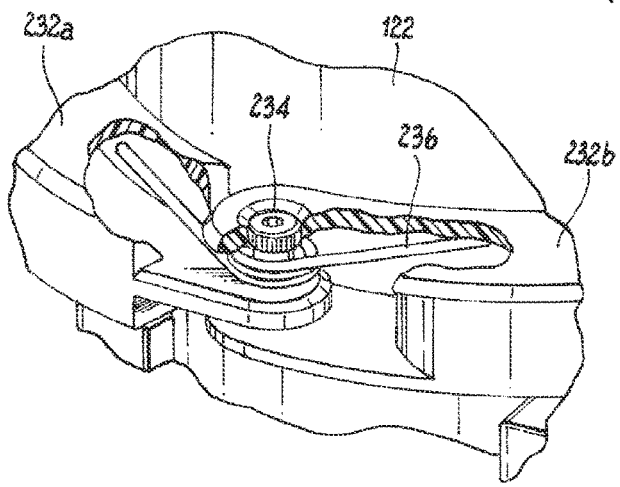
FIG. 39 is an enlarged localized view of the hinge of the spring biased buckle of the gas sealed access cap shown in FIG. 37.

Referring now to FIGS. 37 through 40, there is illustrated an attachment mechanism for releasably attaching an embodiment of the gas sealed access cap 26 to the proximal bowl portion 110 of robotic cannula 28, which is defined by a spring biased and hinged buckle assembly 230. The buckle assembly 230 includes a pair of C-shaped buckle portions 232a, 232b that are hingedly attached to one another about a pivot pin 234, as best seen in FIG. 39. The buckle assembly 230 can be supported on the lower annular flange 224 of the main housing portion 122 of access cap 26, or it could be a separate component.

Figure 37:
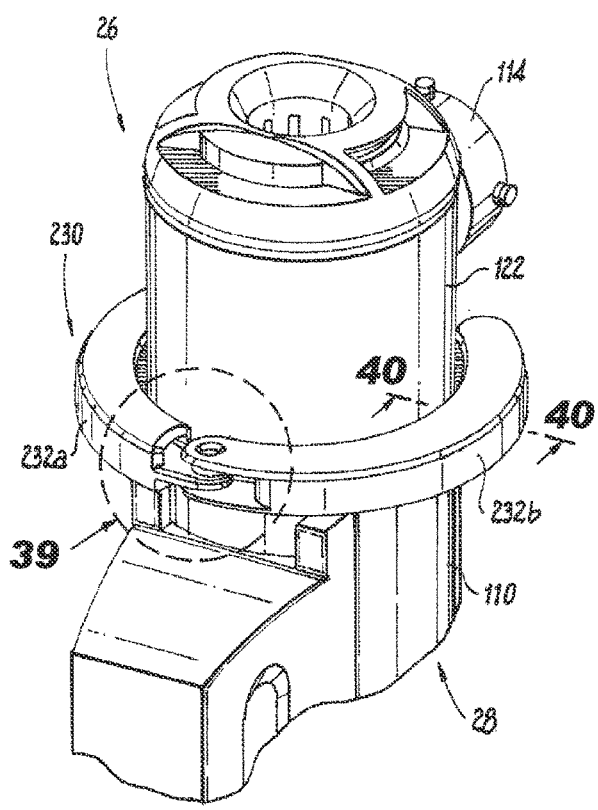
FIG. 37 is a perspective view of the gas sealed access cap of the subject invention with a spring biased buckle for detachably engaging the access cap to the proximal housing of a robotic cannula.
Figure 38:
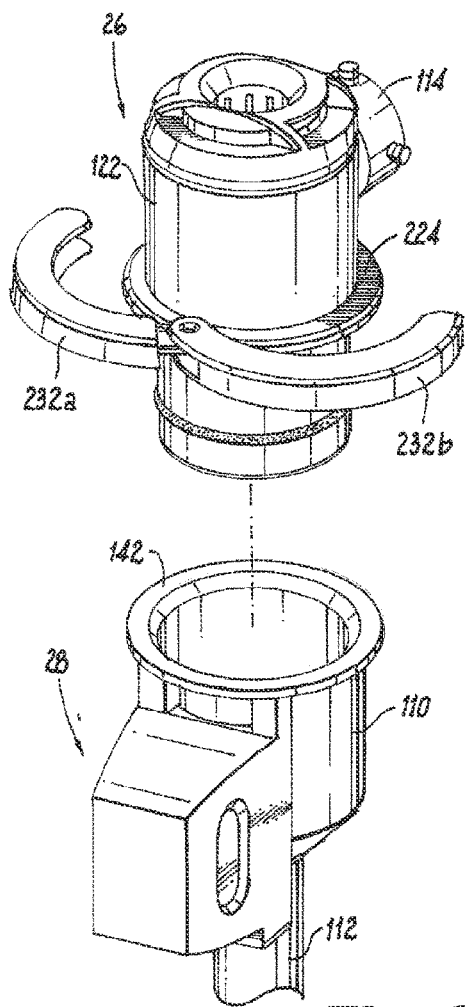
FIG. 38 is a perspective view of the gas sealed access cap shown in FIG. 37, separated from the proximal housing of the robotic cannula.
Figure 40:
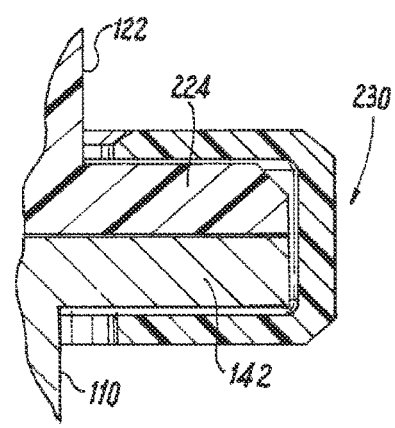
FIG. 40 is a cross-sectional view taken along line 40-40 of FIG. 37.

The two buckle portions 232a, 232b are normally biased toward one another into a closed and locked position shown in FIG. 37, by a torsion spring 236 that is associated with pivot pin 234. The buckle assembly 230 is adapted and configured for manual movement between an open position shown in FIG. 38 that allows for easy manual separation of the gas sealed access cap 26 from the bowl portion 110 of robotic cannula 28, and the closed position shown in FIG. 37, wherein the buckle portions 232a, 232b close around the annular flange 224 on the main housing portion 122 of the access cap 26 and the proximal flange 142 of the bowl portion 110 of robotic cannula 28 to securely retain them by way of a friction fit, as best seen in FIG. 40. Those skilled in the art will readily appreciate that the buckling attachment feature shown in FIGS. 37 through 40 can be employed with the valve sealed access cap 30 in accordance with the subject invention.

Referring now to FIGS. 41 through 43, there is illustrated another attachment mechanism for releasably attaching an embodiment of the gas sealed access cap 26 to the proximal bowl portion 110 of robotic cannula 28, which is defined by a magnetic skirt assembly 240. The magnetic skirt assembly 240 includes a magnetic ring 242 that can be over-molded onto the underside of the housing flange 224 so that it can interact directly with the metallic proximal flange 142 of the bowl portion 110 of cannula 28, as best seen in FIG. 42. Alternatively, the magnetic ring 242 could be ultrasonically welded between two clipless plastic skirts 244 and 246, and then together the assembly can be secured to the undersurface of annular flange 224 of housing 122, as shown in FIG. 43. Those skilled in the art will readily appreciate that the magnetic attachment feature shown in FIGS. 41 through 43 can be employed with the valve sealed access cap 30 in accordance with the subject invention.

Figure 36:
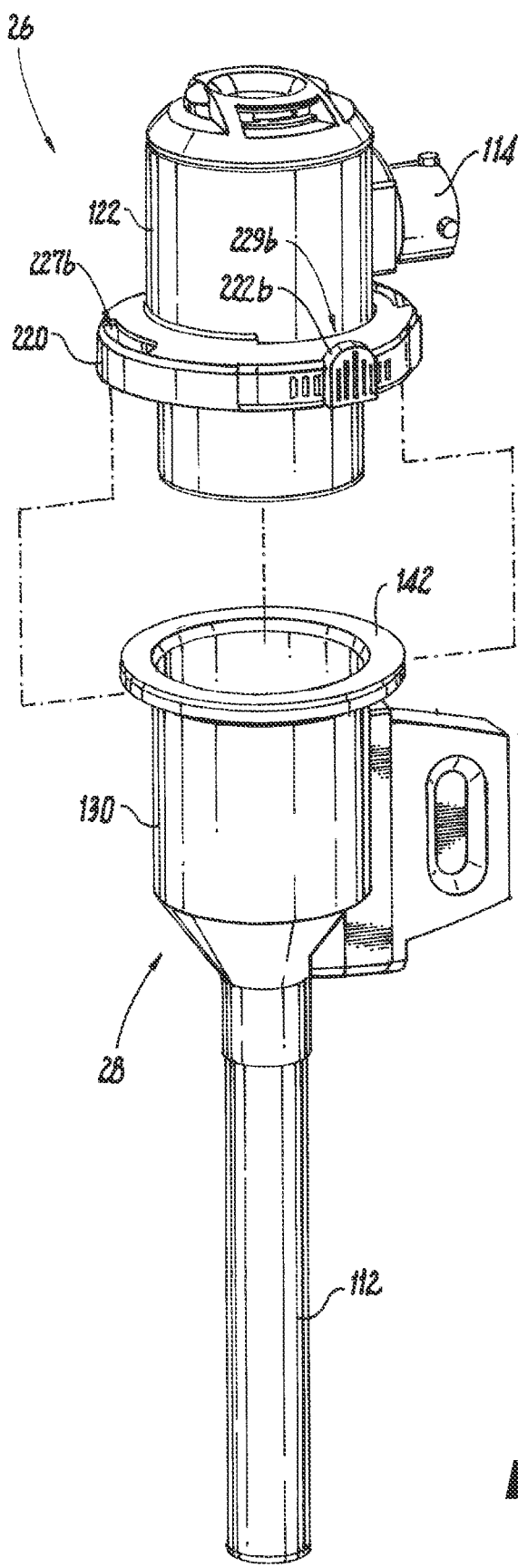
FIG. 36 is a perspective view of the gas sealed access cap shown in FIG. 31, separated from the proximal housing of the robotic cannula.
Figure 44:
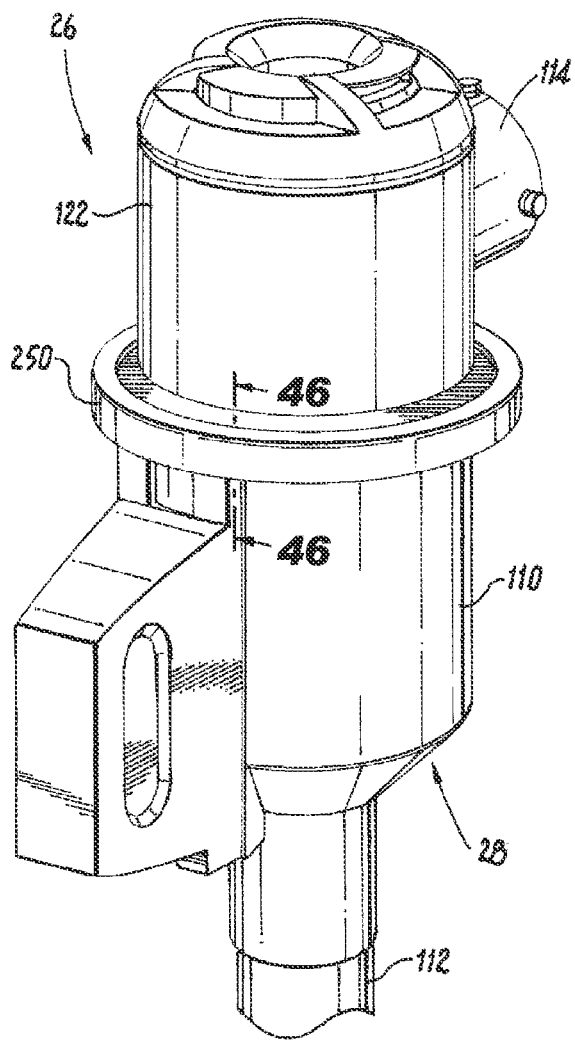
FIG. 44 is a perspective view of the gas sealed access cap of the subject invention with an axially movable inverted compressible skirt for detachably engaging the access cap to the proximal housing of a robotic cannula.
Figure 45:
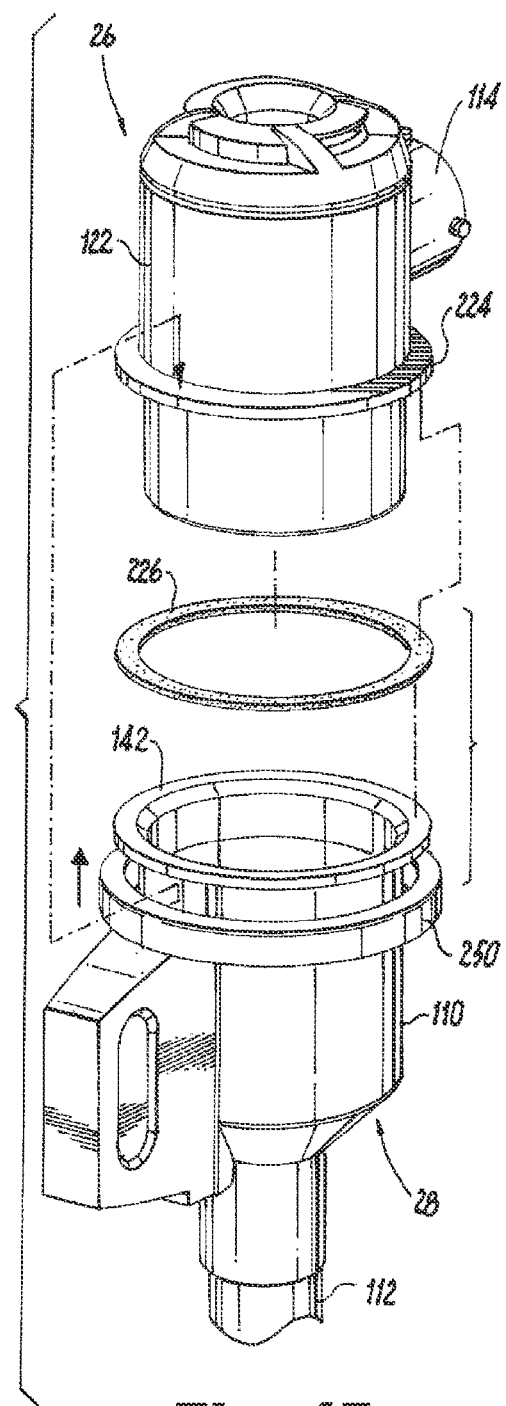
FIG. 45 is an exploded perspective view the gas sealed access cap of FIG. 44 with parts separated for ease of illustration.
Figure 46:
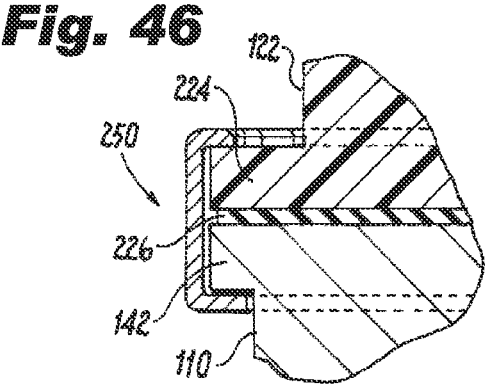
FIG. 46 is a cross-sectional view taken along line 46-46 of FIG. 44.

Referring to FIGS. 44 through 46, there is illustrated an attachment mechanism for releasably attaching an embodiment of the gas sealed access cap 26 to the proximal bowl portion 110 of robotic cannula 28, which is defined by a compressible pinch skirt 250 similar in construction and function to that which is illustrated in FIG. 36, but in this embodiment of the invention, which is shown schematically, the compressible pinch skirt 250 is inverted and mounted for axial movement relative to the bowl portion 110 of cannula 28, as best shown in FIG. 45.

More particularly, the axially movable inverted pinch skirt 250 can be raised and lowered relative to the bowl portion 110 of robotic cannula 28 to facilitate the releasable attachment of the gas sealed access cap 26 to the robotic cannula 28. Those skilled in the art will readily appreciate that the movable pinch skirt feature shown in FIGS. 44 through 46 can be employed with the valve sealed access cap 30 in accordance with the subject invention.

Figure 47:
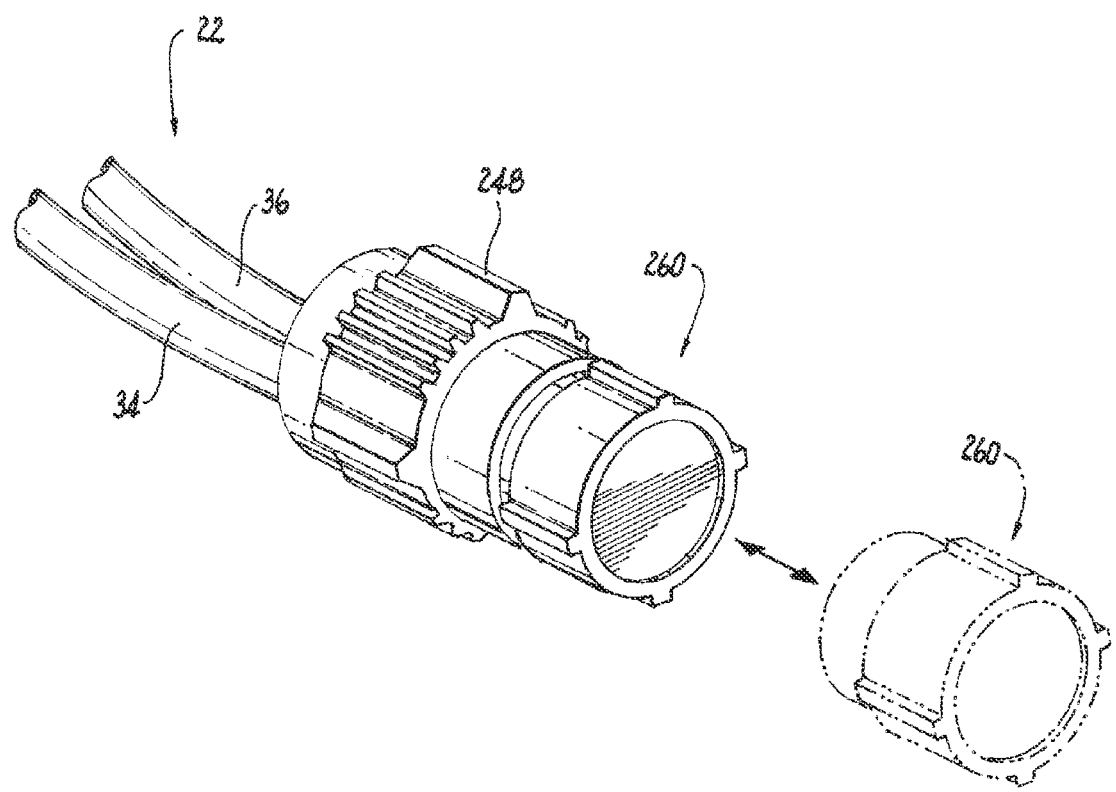
FIG. 47 is a perspective view of a bulls-eye connector plug for engaging a tri-lumen connector associated with the distal end of the dual lumen portion of the filtered tube set of the subject invention.

Referring now to FIG. 47, there is illustrated a tri-lumen bullseye plug 260 that is adapted and configured to intimately mate with the tri-lumen bullseye connector fitting 248 associated with the dual lumen portion 22 of tube set 20, shown in FIG. 22. The bullseye plug 260 is utilized when the dual lumen portion 22 of tube set 20 is not being employed, but the single lumen portion 24 of tube set 20 is being employed, such as, for example, during an initial insufflation stage of a robotically assisted surgical procedure. When it is installed, the bullseye plug 260 creates a negative pressure in the dual lumen portion 22 of tube set 20 that indicates to a pressure sensor in the gas delivery system 12 that a standard insufflation mode is underway. At such a time, the pump 16 within the gas delivery system 12 will be inactive.

Figure 48:
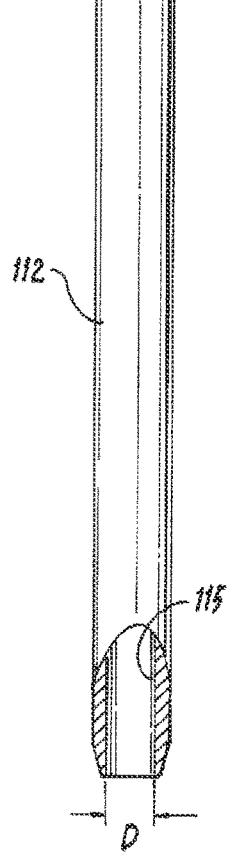
FIG. 48 is a side elevational view of a conventional Da Vinci Xi robotic cannula, which has a tubular body portion having an inner diameter that is dimensioned to accommodate the shaft of a robotic surgical instrument.

Turning now to FIG. 48, there is illustrated in fine detail the Da Vinci robotic cannula 28 employed with the gas sealed access cap 26 of the subject invention, as previously illustrated for example in FIG. 1. As can be readily seen, the elongated body portion 112 of robotic cannula 28 has an internal bore 115 with an inner diameter D that is about 8.89 mm, and it is dimensioned to accommodate the shaft of a robotic instrument having an outer diameter of about 8.55 mm, which is not shown. This allows for a 0.39 mm gap therebetween for gas flow. However, a greater gap is needed for the gas sealed access cap 26 to function effectively. In order to enhance the functionality of the gas sealed access cap 26 of the subject invention, a cannula with a larger inner diameter is required, so that pressurized gas can flow more readily between the inner periphery of the internal bore 115 and the outer periphery of a robotic instrument extending therethrough.

Figure 49:
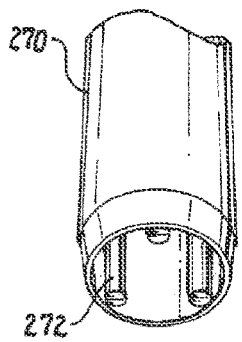
FIG. 49 is a perspective view of the distal end portion of the tubular body of a modified robotic cannula which has an expanded inner diameter with a plurality of circumferentially spaced apart elongated beads for creating interior flow channels for gas.
Figure 50:
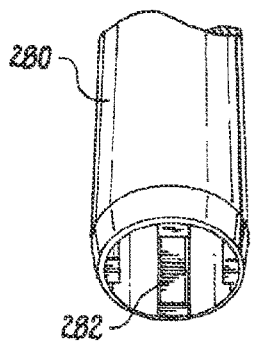
FIG. 50 is a perspective view of the distal end portion of the tubular body of a modified robotic cannula which has an expanded inner diameter with a plurality of circumferentially spaced apart elongated channels formed in the interior surface of the tubular body for gas flow.
Figure 51:
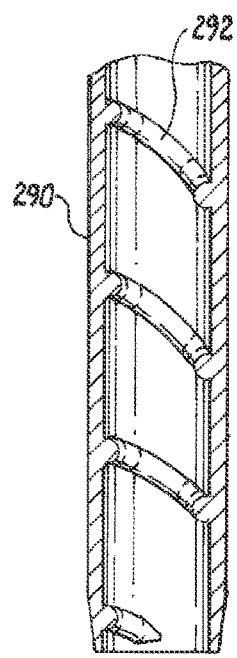
FIGS. 51 and 52 are cross-sectional views of the tubular body of a modified robotic cannula which has a helical bead formed on the interior surface thereof forming a helical flow passage for gas.
Figure 52:
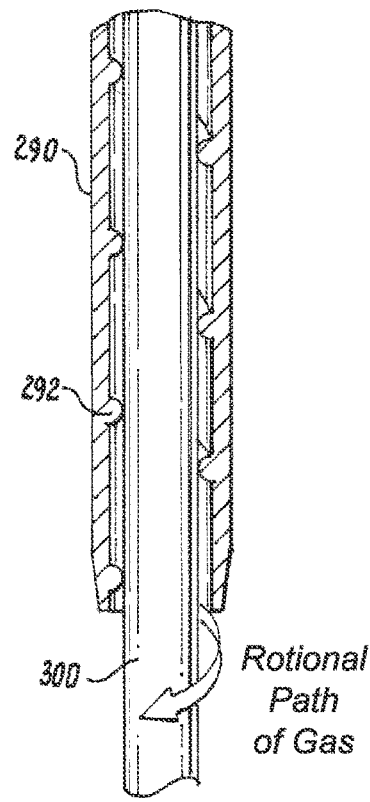

In this regard, FIG. 49 illustrates a robotic cannula body 270 having a set of circumferentially spaced apart linear beads 272 that are formed or otherwise provided on the interior surface thereof to provide enhanced gas flow for the gas sealed access cap 26. Similarly, FIG. 50 illustrates a robotic cannula body 280 having a set of circumferentially spaced apart linear channels 284 that are formed in the interior surface thereof to provide enhanced gas flow for the gas sealed access cap 26. Finally, FIG. 51 illustrates a robotic cannula body 290 having a continuous helical bead 292 that is formed or otherwise provided on the interior surface thereof to provide enhanced gas flow between the interior wall of the cannula body 290 and a robotic instrument 300 extending therethrough, as best seen in FIG. 52. Those skilled in the art will readily appreciate that these features of the cannula body could also provide enhanced gas flow when used in conjunction with the valve sealed access cap 30.

While the gas circulation system of the subject disclosure has been shown and described with reference to preferred embodiments, those skilled in the art will readily appreciate that changes and/or modifications may be made thereto without departing from the scope of the subject disclosure.

What is claimed is:

1. A gas sealed access cap for a robotic cannula comprising:
   a) a housing comprising an inlet port, an outlet port, and an interior cavity, the housing having a lid defining a central access port configured to extend to the interior cavity, the interior cavity configured to support an annular jet assembly, the annular jet assembly configured for receiving pressurized gas from the inlet port of the housing, wherein the annular jet assembly includes a central aperture configured to be aligned with the central access port of the lid and is adapted to generate a gaseous sealing zone within the robotic cannula to maintain a stable pressure within the surgical cavity of a patient;
   b) a plurality of circumferentially spaced apart radially inwardly extending vanes formed integral with the housing and located within the interior cavity, the vanes being configured for directing spent gas from the gaseous sealing zone to the outlet port of the housing; and
   c) a central access tube configured to be aligned with the central access port of the lid and the central aperture of the annular jet assembly, and extending distally from the interior cavity of the housing below the vanes for communicating with a tubular portion of the robotic cannula, wherein the housing of the access cap is dimensioned and configured for reception within a proximal bowl portion of the robotic cannula.

2. The gas sealed access cap recited in claim 1, further comprising a pair of diametrically opposed flexible clips, wherein the pair of diametrically opposed flexible clips are formed integral with an exterior surface of the housing for releasably securing the access cap to the proximal bowl portion of the robotic cannula.

3. The gas sealed access cap recited in claim 1, further comprising a sound attenuating disc, wherein the sound attenuating disc is configured to be positioned within the housing between the lid and the annular jet assembly.

4. The gas sealed access cap recited in claim 3, wherein the sound attenuating disc is formed from a foam material.

5. The gas sealed access cap recited in claim 1, further comprising a mounting flange, wherein the inlet port of the housing and the outlet port of the housing are positioned within the mounting flange, and the mounting flange is formed on an exterior surface of the housing.

6. The gas sealed access cap recited in claim 5, further comprising a manifold, wherein the manifold is configured to be operatively associated with the mounting flange.

7. The gas sealed access cap recited in claim 6, wherein the manifold is formed separate from the housing of the access cap.

8. The gas sealed access cap recited in claim 6, wherein the manifold includes a multi-lumen bullseye connector.

9. The gas sealed access cap recited in claim 1, wherein a distal end of the housing extends distally beyond a distal end of the central access tube.

10. The gas sealed access cap recited in claim 1, wherein a distal end of the central access tube extends distally beyond a distal end of the housing.

11. The gas sealed access cap recited in claim 1, further comprising an outer O-ring seal, wherein the outer O-ring seal is configured to surround a distal portion of the housing to provide a seal between the housing and the proximal bowl portion of the robotic cannula.

12. A gas sealed access cap for a robotic cannula comprising:
    a) a housing comprising an inlet port, an outlet port, and an interior cavity, the housing having a lid defining a central access port configured to extend to the interior cavity, the interior cavity configured to support an annular jet assembly, the annular jet assembly configured for receiving pressurized gas from the inlet port of the housing, wherein the annular jet assembly includes a central aperture configured to be aligned with the central access port of the lid and is adapted to generate a gaseous sealing zone within the robotic cannula to maintain a stable pressure within the surgical cavity of a patient;
    b) a plurality of circumferentially spaced apart radially inwardly extending vanes formed integral with the housing and located within the interior cavity, the vanes being configured for directing spent gas from the gaseous sealing zone to the outlet port of the housing; and
    c) a central access tube configured to be aligned with the central access port of the lid and the central aperture of the annular jet assembly, and extending distally from the interior cavity of the housing below the vanes for communicating with a tubular portion of the robotic cannula, wherein a distal end of the central access tube extends distally beyond a distal end of the housing and wherein the housing of the access cap is dimensioned and configured for reception within a proximal bowl portion of the robotic cannula.

13. The gas sealed access cap recited in claim 12, further comprising a pair of diametrically opposed flexible clips, wherein the pair of diametrically opposed flexible clips are formed integral with an exterior surface of the housing for releasably securing the access cap to the proximal bowl portion of the robotic cannula.

14. The gas sealed access cap recited in claim 12, further comprising a sound attenuating disc, wherein the sound attenuating disc is configured to be positioned within the housing between the lid and the annular jet assembly.

15. The gas sealed access cap recited in claim 14, wherein the sound attenuating disc is formed from a foam material.

16. The gas sealed access cap recited in claim 12, further comprising a mounting flange, wherein the inlet port of the housing and the outlet port of the housing are positioned within the mounting flange, and the mounting flange is formed on an exterior surface of the housing.

17. The gas sealed access cap recited in claim 16, further comprising a manifold, wherein the manifold is configured to be operatively associated with the mounting flange.

18. The gas sealed access cap recited in claim 17, wherein the manifold is formed separate from the housing of the access cap.

19. The gas sealed access cap recited in claim 17, wherein the manifold includes a multi-lumen bullseye connector.

20. The gas sealed access cap recited in claim 12, further comprising an outer O-ring seal, wherein the outer O-ring seal is configured to surround a distal portion of the housing to provide a seal between the housing and the proximal bowl portion of the robotic cannula.

* * * * *